(12) United States Patent
Heinrichs et al.

(10) Patent No.: US 8,637,657 B2
(45) Date of Patent: Jan. 28, 2014

(54) SIDEROPHORE-MEDIATED IRON UPTAKE IN BACTERIAL INFECTION

(76) Inventors: David E. Heinrichs, London (CA); Federico Beasley, London (CA); Enríque Vines, London (CA); Johnson Cheung, London (CA)

( * ) Notice: Subject to any disclaimer, the term of this patent is extended or adjusted under 35 U.S.C. 154(b) by 31 days.

(21) Appl. No.: 13/059,723

(22) PCT Filed: Aug. 14, 2009

(86) PCT No.: PCT/CA2009/001143
§ 371 (c)(1),
(2), (4) Date: Jun. 15, 2011

(87) PCT Pub. No.: WO2010/020036
PCT Pub. Date: Feb. 25, 2010

(65) Prior Publication Data
US 2011/0245321 A1  Oct. 6, 2011

Related U.S. Application Data

(60) Provisional application No. 61/136,213, filed on Aug. 19, 2008.

(51) Int. Cl.
C07H 21/04 (2006.01)
C12N 15/85 (2006.01)
C12N 9/00 (2006.01)
C07H 21/02 (2006.01)

(52) U.S. Cl.
USPC ......... 536/24.5; 435/183; 435/325; 536/23.1; 536/24.32; 536/24.3

(58) Field of Classification Search
None
See application file for complete search history.

(56) References Cited

FOREIGN PATENT DOCUMENTS

WO   WO 2006/043182 A2   4/2006

OTHER PUBLICATIONS

Cotton, et al., "Identification and Characterization of the *Staphylococcus aureus* Gene cluster coding for Staphyloferrin" *Biochemistry*, vol. 48(5), p. 1025-1035 (online pub. Dec. 1, 2009), ISSN: 1520-4995.

Cheung, et al., "Molecular Characterization of Staphyloferrin B Biosynthesis in *Staphylococcus aureus*", *Mol. Microbiol.*, (online pub. Sep. 22, 2009), ISSN: 1365-2958.

Beasley, et al., "Characterization of A Biosynthetic and Transport Mutants in *Staphylococcus aureus*", *Mol. Microbiol.*, vol. 72(4), p. 947-963 (online pub. Apr. 14, 2009), ISSN: 1365-2958.

Ferreras, et al., "Small-molecule Inhibition of Siderophore Biosynthesis in *Mycobacterium tuberculosis* and *Yersinia pestis*", *Nat. Chem. Biol.*, vol. 1(1), p. 29-32 (online pub. May 24, 2005), ISSN: 1552-4450.

Dale, et al., "Role of Siderophore Biosynthesis in Virulence of ; Identification and Characterization of Genes Involved in Production of a Siderophore", *Infect. Immun.*, vol. 72(1), p. 29-37 (Jan. 2004), ISSN: 0019-9567.

*Primary Examiner* — Amy Bowman

(57) ABSTRACT

The present invention relates to methods of inhibiting *S. aureus* comprising inhibiting siderophore-mediated iron uptake, for example, staphyloferrm-mediated iron uptake Such methods of inhibiting *S. aureus* include the inhibition of staphyloferrm A- and staphyloferrm B-mediated uptake either by inhibiting expression or activity of staphyloferrm A and B or by inhibiting transport of staphyloferrm A and B The methods as provided would be useful for treating *S. aureus* infection.

11 Claims, 19 Drawing Sheets

A

CATAATTCACCTCTATGAAATATTTTACAAAAGCAAGATAGATTTGTATA
GTATTAAGTGGAGATACTTTATAAAATGTTTTCGTTCTATCTAAACATAT
Met        S.D.
←*NWMN_2082*

Fur box              S.D.
ATCCATATTAATGATAATGATTCTTATTATCAACAGAATGCGGGTGTAAG
TAGGTATAATTACTATTACTAAGAATAATAGTTGTCTTACGCCCACATTC

*NWMN_2081→*
   Met
TTTTATG (SEQ ID No:25)
AAAATAC (SEQ ID No:26)

B

*NWMN_2079 stop*
TAATGAAATCTCCTGCTATGGTAAACCACTATTAATATATTTATCAATAA
ATTACTTTAGAGGACGATACCATTTGGTGATAATTATATAAATAGTTATT GTCTAAGTTGACAAGTTATACTACATATCGTTTGCACGGTTGTATCATAA
CAGATTCAACTGTTCAATATGATGTATAGCAAACGTGCCAACATAGTATT TTGTTCAACTTAGATTTTTTGTATTTGTTGATTTATCAAATTAAGTGCAA
AACAAGTTGAATCTAAAAAACATAAACAACTAAATAGTTTAATTCACGTT CAGTTCGTTCACATAAAATTGCAACAGATAATATCAGCTGAATTACAGGGA
GTCAAGCAGTGTATTTTAACGTTGTCTATTATAGTCGACTTAATGTCCCT TAACGGTCATGCTAAATGGTGTCAATTGTATTAATGCAAAGATGATATAG
ATTGCCAGTACGATTTACCACAGTTAACATAATTACGTTTCTACTATATC CAATGATACATTATCAGTATTTTGTCTAAGCAAATGTGCTAATTGTAGTC
GTTACTATGTAATAGTCATAAAACAGATTCCTTTACACGATTAACATCAG ATAATTATTAGAGGAAATATATAGTCATACATTTTAGAAATATAAAAAAG
TATTAATAATCTCCTTTATATATCAGTATGTAAAATCTTTATATTTTTTC Fur box
ATTGAACGTTACTTGACAATGATAATTGTTATCAATAAAATAATAAATGA
TAACTTGCAATGAACTGTTACTATTAACAATAGTTATTTTATTATTTACT

*htsA→*
            S.D.        Met
AGTTATACATATTAAGGAGTGGAACGATG (SEQ ID No:27)
TCAATATGTATAATTCCTCACCTTGCTAC (SEQ ID No:28)

Fig. 4

A
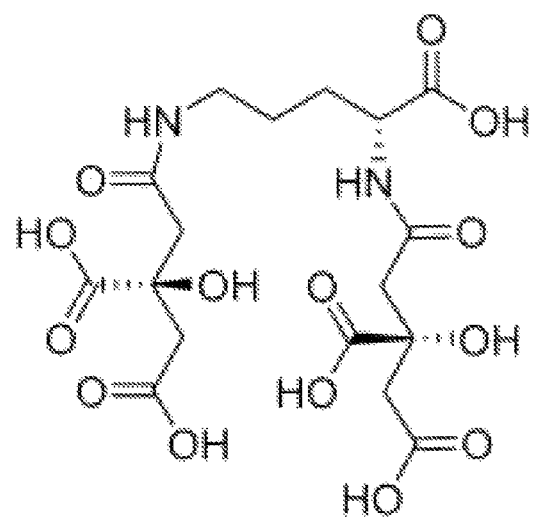
B
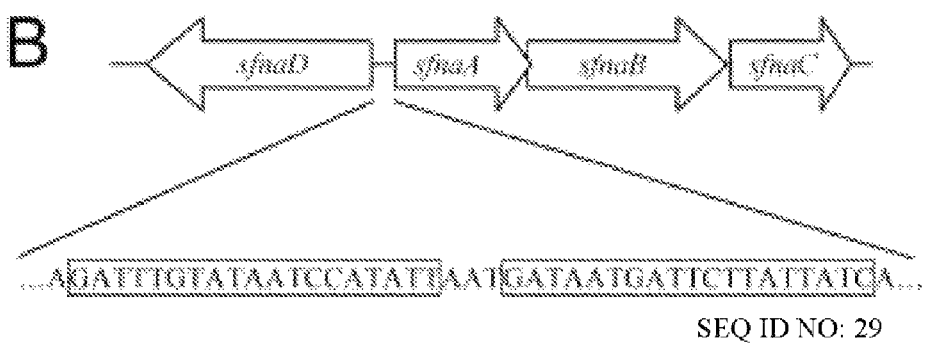
SEQ ID NO: 29
Fig. 17

SIDEROPHORE-MEDIATED IRON UPTAKE IN BACTERIAL INFECTION

PRIORITY CLAIMS AND RELATED APPLICATIONS

This application claims the benefit of U.S. Provisional Application No. 61/136,213, filed Aug. 19, 2008.

FIELD OF INVENTION

The present invention relates to iron uptake pathways in infectious bacteria, and in particular, to methods of utilizing siderophore-mediated iron uptake pathways to inhibit such bacteria.

BACKGROUND OF THE INVENTION

With few exceptions, iron is an essential nutrient for all microbes. Under physiological conditions, iron persists predominantly in insoluble ferric (Fe3+) hydroxides and is typically complexed to proteins for transport and storage through animal fluids. Intracellular iron is borne by ferritins, a phylogenetically ubiquitous class of globular iron storage proteins, and by heme associated proteins, while serum iron is bound by glycoproteins, principally transferrin. Enhanced iron sequestration, known as hypoferremia, is a facet of the innate immune response that further restricts iron availability to invading pathogens. This arises from endocytosis of ferrated glycoproteins, an increase in hepatically localized ferritin, and restriction of iron release into the extracellular milieu by the reticuloendothelial system. Owing to its low solubility and stringent sequestration, free iron in human tissues is estimated to be around $10^{-18}$ M, well below the threshold required to sustain microbial life, making iron acquisition a major challenge faced by agents of systemic infection.

Numerous bacteria, fungi, and plants overcome iron limitation by secreting siderophores: low molecular weight, high affinity ferrichelators. In mammalian sera, these may compete with transferrin for host iron. Ferrated siderophores are recognized by cognate cell surface receptor proteins and transported through the cytosolic membrane via ATP-binding cassette (ABC) transporters. Siderophore mediated iron uptake makes a significant contribution to the pathogenesis of many Gram-positive and Gram-negative bacterial pathogens, including *Yersinia pestis, Burkholderia cepacia, Pseudomonas aeruginosa*, septicemic *Escherichia coli* and *Staphylococcus aureus*.

*Staphylococcus aureus* (*S. aureus*) is a commensal organism as well as a pathogen of several mammalian species, including humans and cattle. *S. aureus* isolates that caused infection in cows, horses, goats, sheep and camel have been reported. Isolates of zoonotic *S. aureus* in which infection has passed from humans to other animals and vice versa have also been reported.

*S. aureus* is a colonist of human mucosal and epidermal surfaces, and a frequent opportunistic pathogen of surgical wounds and implanted medical devices. *S. aureus* expresses a myriad array of virulence factors, including adhesins, proteases, lysins, and superantigens, many of which act to improve iron availability through processes such as erythrolysis. Systemic dissemination through blood and soft tissues is characterized by rapid bacterial proliferation and tissue destruction, manifesting in syndromes including septicemia, endocarditis, and necrotizing pneumonia. Coordinated expression of a broad swath of staphylococcal virulence factors takes its cue from iron restriction, a phenomenon mediated by the ferric uptake regulator, Fur. This DNA binding protein recognizes $Fe^{2+}$ as a repressive cofactor. Plunging levels of soluble iron lead to its dissociation from cognate Fur boxes in operator regions of the iron responsive regulon and derepression of transcription.

*S. aureus* is a prevalent human pathogen that causes a wide range of infections ranging from minor skin lesions, impetigo and food poisoning to more serious diseases such as sepsis, endocarditis, osteomyelitis, pneumonia, bacteremia, and toxic shock syndrome. Initially, penicillin could be used to treat even the worst *S. aureus* infections. However, the emergence of penicillin-resistant strains of *S. aureus* has reduced the effectiveness of penicillin in treating *S. aureus* infections and most strains of *S. aureus* encountered in hospital infections today do not respond to penicillin.

Methicillins, introduced in the 1960s, largely overcame the problem of penicillin resistance in *S. aureus*. However, methicillin resistance has emerged in *S. aureus*, along with resistance to many other antibiotics effective against this organism, including vancomycin, aminoglycosides, tetracycline, chloramphenicol, macrolides and lincosamides. In fact, methicillin-resistant strains of *S. aureus* generally are multiply drug resistant. Methicillian-resistant *S. aureus* (MRSA) has become one of the most important nosocomial pathogens worldwide and poses serious infection control problems. Drug resistance of *S. aureus* infections poses significant treatment difficulties, which are likely to get much worse unless new therapeutic agents are developed.

Accordingly, it would be desirable to develop novel methods of treating *S. aureus* infection based on a more thorough understanding of the essential iron-uptake pathways in this organism.

SUMMARY OF THE INVENTION

The genes and proteins involved in the siderophore-mediated iron uptake of *S. aureus* have now been determined, and are useful for the provision of novel methods to treat *S. aureus* infection.

Accordingly, in one aspect of the invention, a method of inhibiting *S. aureus* is provided comprising inhibiting staphyloferrin-mediated iron uptake.

In another aspect of the invention, methods of making staphyloferrins, including staphyloferrin A and staphyloferrin B, are provided comprising incubating Sbn/Sbt polypeptides with staphyloferrin-producing substrates to yield functional staphyloferrin.

These and other aspects of the invention are described in the detailed description that follows by reference to the following drawings.

BRIEF DESCRIPTION OF THE DRAWINGS

FIG. 4 provides an intergenic region between sbtA and sbtBCD coding regions (A) and an intergenic region between sbtD and htsABC coding regions (B) identifying putative Fur box sequences, start codons for the sbtA, sbtB and htsA genes (boldface) and Shine-Dalgarno sequences (S.D.);

FIG. 17 illustrates the structure of staphyloferrin A;

DETAILED DESCRIPTION OF EMBODIMENTS

Figure 1:
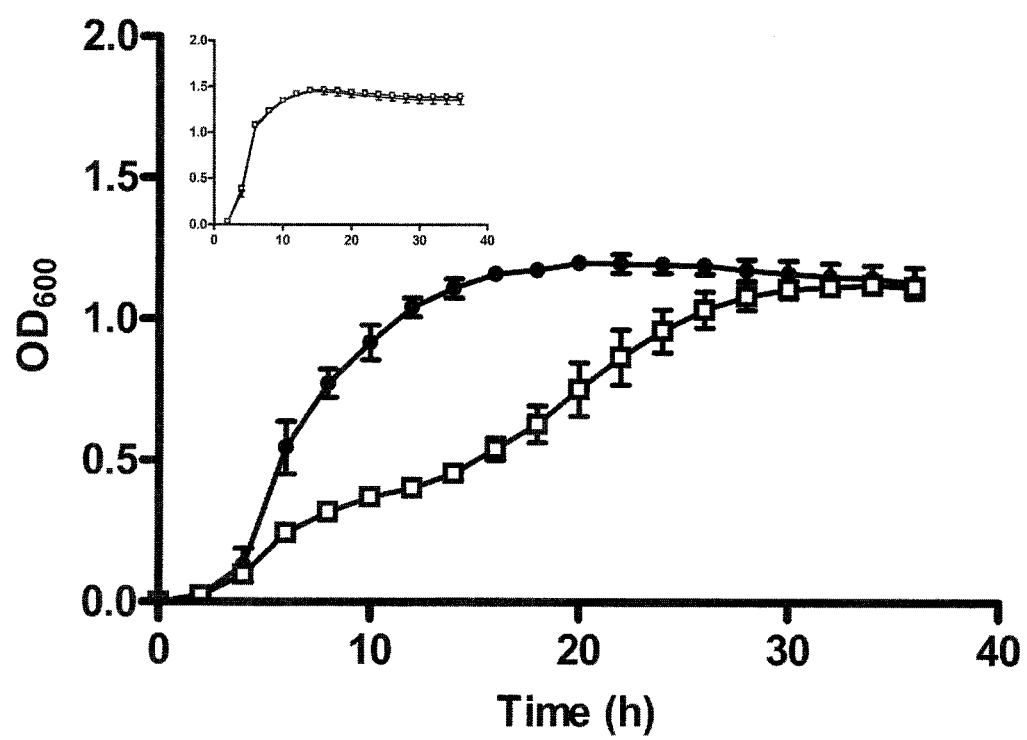
FIG. 1 graphically illustrates impaired growth of *S. aureus* sbn operon deletion strain in serum, and the inset graphically illustrates growth of the deletion strain in serum supplemented with $FeCl_3$.

A method of inhibiting *S. aureus* is provided comprising inhibiting siderophore-mediated iron uptake, for example, staphyloferrin-mediated iron uptake.

Siderophore-mediated iron uptake encompasses siderophore biosynthesis and/or siderophore uptake or transport. Two paths of siderophore biosynthesis and uptake have now been identified. In one path, the siderophore, staphyloferrin A, is produced by Sbt polypeptides and transported for cellular uptake by Hts polypeptides. In another path, the siderophore, staphyloferrin B, is produced by Sbn polypeptides and transported for cellular uptake by Sir polypeptides The terms "staphyloferrin A" and "staphyloferrin B" refer to high affinity α-hydroxycarboxylate iron-chelating compounds or siderophores of *S. aureus* which bind iron, generally in the form of ferric ($Fe^{3+}$) ions. The structure of staphyloferrin A is provided in FIG. 17 while the structure of staphyloferrin B is provided in FIG. 16.

Staphyloferrin A is produced by Sbt polypeptides expressed from a gene cluster referred to herein as the "sbt" or "sfna" gene cluster, and transported into the cell by HtsABC polypeptides expressed from hts genes.

The "sbt" or "sfa" gene cluster refers to a group of *S. aureus* genes, namely, sbtA, sbtB, sbtC, and sbtD that have been isolated from a common chromosomal locus and respectively encode polypeptides SbtA, SbtB, SbtC and SbtD which are involved in the biosynthesis of staphyloferrin A. In one embodiment, SbtB and SbtD are NIS (NRPS-independent siderophore) synthetases, SbtC is an amino acid racemase and SbtA is a membrane embedded siderophore efflux protein. Exemplary nucleotide sequences of sbt genes and corresponding encoded Sbt polypeptides may be found in GenBank accession number AP009351 or RefSeq accession number NC_009641 at loci NWMN_2079, NWMN_2080, NWMN_2081 and NWMN_2082. Exemplary amino acid sequences of Sbt polypeptides may also be found at GenBank Protein ID accession numbers BAF68351, BAF68352, BAF68353 and BAF68354.

It has been determined that staphyloferrin A may be synthesized outside of its native environment, for example, recombinantly in bacteria in which it is not endogenously expressed, as well as under cell-free conditions. Thus, in one embodiment, sbt genes may be transfected into selected bacterial cells, using established technology, and incubated in media including Sbt substrates, e.g. (e.g. citrate, D-ornithine) and cofactors (ATP and $Mg^{2+}$) for expression to yield functional staphyloferrin A. In another embodiment, Sbt polypeptides, including SbtA, SbtB, SbtC and SbtD, may be incubated in a cell-free environment under conditions designed to emulate the basic functional biochemistry of the cell, for example, including a carboxylate substrate such as citric acid and D-ornithine to yield functional staphyloferrin A. In a further embodiment, Sbt synthetases, such as SbtB and SbtD alone, may be incubated in the presence of a carboxylate substrate such as citric acid and D-ornithine to yield functional staphyloferrin A. If D-ornithine is substituted with L-ornithine, then SbtC may be added to convert to the D-racemate. In this regard, the sbt genes or Sbt peptides may be derived from any one of *S. aureus*, *S. epidermidis*, *S. haemolyticus* and *S. saprophyticus* sources, or derived from a combination of these sources.

The HtsABC transporter is encoded by an "hts operon" comprising a group of bacterial genes including htsA, htsB, and htsC that share a common promoter. This operon encodes a protein system that functions to transport ferrated siderophore, namely staphyloferrin A, into *S. aureus* cells, also known as an ABC transporter. The promoter element, which is upstream of the htsA coding region, is iron-regulated through the Fur protein. The htsA gene encodes a heme or siderophore binding protein (HtsA), while htsB and htsC encode transmembrane components (HtsB/C) of the ABC-transporter. Exemplary nucleotide sequences of hts genes and corresponding encoded Hts polypeptides may be found in GenBank accession number AP009351 or RefSeq accession number NC_009641 at loci NWMN_2076, NWMN_2077, and NWMN_2078. Exemplary amino acid sequences of Hts polypeptides may also be found at GenBank Protein ID accession numbers BAF68348, BAF68349, and BAF68350. The hts-encoded siderophore transport system interacts with a FhuC ATPase as will be described.

The siderophore, staphyloferrin B, also previously referred to as staphylobactin, an α-hydroxycarboxylate siderophore comprised of L-2,3-diaminopropionic acid, citric acid, ethylenediamine and α-ketoglutaric acid, is produced by a gene cluster referred to as the "sbn" gene cluster. Ferrated staphyloferrin B is transported into the organism via a SirABC transporter system.

The "sbn" gene cluster refers to a group of S. aureus genes, namely, sbnA, sbnB, sbnC, sbnD, sbnE, sbnF, sbnG, sbnH, and sbnI that share a common promoter. The promoter element, which is upstream of the sbnA coding region, is iron-regulated. Exemplary nucleotide sequences of sbn genes may be found at Genbank accession no. AY251022. The sbn genes respectively encode the polypeptides "SbnA", "SbnB", "SbnC", "SbnD", "SbnE", "SbnF", "SbnG", "SbnH", and "SbnI" which are involved in the synthesis of staphyloferrin B. Sequence information for these polypeptides may be found in published PCT application, WO 06/043182. Accordingly, in one embodiment, sbnA encodes a cysteine synthase, sbnB encodes an ornithine cyclodeaminase, sbnC encodes a biosynthesis protein, sbnD encodes an efflux protein, sbnE encodes a siderophore biosynthesis protein, sbnF encodes a siderophore biosynthesis protein, sbnG encodes an aldolase protein, and sbnH encodes an amino acid decarboxylase.

It has been determined that staphyloferrin B may be synthesized outside of its native environment, for example, recombinantly in bacteria in which it is not endogenously expressed, as well as under cell-free conditions. Thus, in one embodiment, sbn genes may be transfected into selected bacterial cells, using established technology, and incubated in media including Sbn substrates, (e.g. citrate, L-2,3-diaminopropionic acid, alpha-ketoglutarate, ATP, $Mg^{2+}$) for expression to yield functional staphyloferrin B. In another embodiment, Sbn polypeptides, including SbnA, SbnB, SbnC, SbnD, SbnE, SbnF, SbnG, SbnH and SbnI, may be incubated with suitable Sbn substrates in a cell free environment under conditions designed to emulate the basic functional biochemistry of the cell to yield functional staphyloferrin. In a further embodiment, Sbn synthetases, such as SbnC, SbnE and SbnF, and decarboxylases, such as SbnH, alone may be incubated in the presence of substrates such as: L-2,3-diaminopropionic acid, citric acid, and α-ketoglutaric acid, to yield functional staphyloferrin B.

The SirABC transporter is encoded by a "sirABC operon" comprising a group of genes including sirA, sirB, and sirC that share a common promoter. This operon encodes a protein system that functions to transport ferrated siderophore into S. aureus cells, also known as an ABC transporter. Exemplary nucleotide and polypeptide sequences of sirABC operon, and the Sir proteins it encodes, may be found at GenBank Accession No. AY251022 and GenBank Accession No. AF079518. The sirA gene encodes an extracellular protein (SirA), while sirB and sirC encode transmembrane domains (SirB/SirC) of the ABC-transporter. The term "SirABC iron-siderophore transport system" refers the SirABC transporter that is comprised of SirA, SirB, SirC, and FhuC polypeptides.

FhuC is a polypeptide of the "ferric hydroxamate uptake system" or "fhu system". The fhu system is encoded by five genes: fhuC, fhuB, and fhuG, and fhuD1 and fhuD2. fhuC, fhuB, and fhuG are present in an operon (fhuCBG operon) and encode components of an ATP-binding cassette (ABC) transporter. fhuC encodes an ATPase that interacts with both sir and hts encoded siderophore transport systems. fhuD1 and fhuD2 are separately encoded and encode lipoproteins that bind ferric hydroxamate complexes with high affinity. Exemplary nucleotide and amino acid sequences for the fhuCBG operon may be found in GenBank, Accession Nos. AF251216, AAF98153, AAF98154, and AAF98155; for fhuD1, Accession No. AF325854 and AAK92085; and for fhuD2 AF325855 and AAK92086. The terms "FhuC", "FhuB", "FhuG", "FhuD1", and "FhuD2" refer to the proteins encoded by fhuC, fhuB, fhuG, fhuD1 and fhuD2, respectively.

In accordance with an aspect of the invention, S. aureus may be inhibited by inhibiting staphyloferrin-mediated iron uptake, i.e. staphyloferrin A-mediated iron uptake and staphyloferrin B-mediated iron uptake. The term "inhibited" as used herein with respect to inhibition of S. aureus refers to at least partial growth inhibition, and includes complete growth inhibition, of S. aureus. The term "inhibiting" as used herein with respect to staphyloferrin A and B iron uptake refers to at least partial inhibition, including complete inhibition, of iron uptake by S. aureus, and includes inhibition of siderophore synthesis, secretion of siderophore and cell uptake of siderophore.

Inhibition of staphyloferrin-mediated iron uptake may be achieved by inhibiting the expression or function of at least one of the Sbt polypeptides required for the production of staphyloferrin A, e.g. at least one of SbtA, SbtB, SbtC and SbtD, for example, SbtB and SbtD, and inhibiting the expression or function of at least one of the Sbn polypeptides required for the production of staphyloferrin B, e.g. at least one of SbnA, SbnB, SbnC, SbnD, SbnE, SbnF, SbnG, SbnH, and SbnI, for example, SbnC, SbnE, SbnF and SbnH. At the nucleic acid level, Sbt/Sbn expression may be blocked using well-established methods in the art including, for example, antisense and RNA interference technologies (siRNA, shRNA and microRNA) to prevent siderophore synthesis. At the protein level, the function of one or more of the Sbt polypeptides and one or more of the Sbn polypeptides may be inhibited to prevent synthesis of each siderophore.

The term "antisense oligonucleotide" as used herein means a nucleotide sequence that is complementary to a target sbt/sbn nucleic acid sequence. The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine and 2-aminoadenine. Other antisense oligonucleotides of the invention may contain modified phosphorous, oxygen heteroatoms in the phosphate backbone, short chain alkyl or cycloalkyl intersugar linages or short chain heteroatomic or heterocyclic intersugar linkages. For example, the antisense oligonucleotides may contain phosphorothioates, phosphotriesters, methyl phosphonates, and phophorodithioates. The antisense oligonucleotides of the invention may also comprise nucleotide analogs that may be better suited as therapeutic or experimental reagents. An example of an oligonucleotide analogue is a peptide nucleic acid (PNA) in which the deoxribose (or ribose) phosphate backbone in the DNA (or RNA), is replaced with a polymide backbone which is similar to that found in peptides. Suitable antisense oligonucleotides will be at least 5 nucleotides in length, and preferably at least about 15 nuceotides long, and will be sufficient to prevent transcription of a target gene to yield functional protein.

In another embodiment, RNA interference technologies (such as siRNA, shRNA and microRNA) may be applied to prevent expression of Sbt/Sbn polypeptides. Application of nucleic acid fragments such as siRNA fragments that correspond with regions of a target sbt/sbn gene, at least to the extent required to bind thereto, may be used to block expression resulting in inhibition of siderophore production. Such blocking occurs when the siRNA fragments bind to the target gene thereby preventing translation of the gene to yield functional Sbt/Sbn polypeptides. Suitable siRNAs are of a length suitable to inhibit expression of a target gene, e.g. at least about 10-15 nucleotides in length, and comprise sufficient complementarity to the target gene to hybridize thereto under desired conditions, e.g. in a cell. The antisense and RNA oligonucleotides may be introduced into tissues or cells using techniques in the art including vectors (retroviral vectors, adenoviral vectors and DNA virus vectors) or physical techniques such as microinjection.

Antisense and RNA oligonucleotides may be constructed using chemical synthesis and enzymatic ligation reactions using procedures known in the art based on sequence information provided. The oligonucleotides may be chemically synthesized using naturally occurring nucleotides or variously modified nucleotides designed to increase the biological stability of the molecules or to increase the physical stability of the duplex formed with mRNA or the native gene, e.g. phosphorothioate derivatives and acridine substituted nucleotides. Alternatively, the oligonucleotides may be produced biologically using recombination technology as is well-established in the art.

Inhibition of Sbt/Sbn polypeptides may be achieved using one or more compounds that interfere with the function of the polypeptide. Thus, given knowledge of the function of a target Sbt/Sbn polypeptide, suitable inhibitory compounds may be identified or developed. For example, the polypeptides SbnC, SbnE and SbnF have been identified as NIS synthetases necessary for staphyloferrin B synthesis. Thus, a compound useful to inhibit such a synthetase would be suitable to inhibit staphyloferrin B synthesis. Inhibition of the decarboxylase activity of SbnH will also inhibit staphyloferrin B synthesis. In this regard, substrate analogs may be useful to block synthetase and/or decarboxylase activity.

Alternatively, Sbt/Sbn polypeptides may be inhibited by limiting access to one or more substrates required for staphyloferrin biosynthesis. In this regard, the enzymes that produce the substrates necessary for staphyloferrin synthesis may be inhibited, for example, inhibition of SbnA or SbnB would inhibit the synthesis of the substrate, diaminopropionic acid, that is required for staphyloferrin B synthesis.

In another embodiment, inhibition of staphyloferrin-mediated iron uptake may be achieved by inhibiting the Hts- and Sir-mediated transport of ferrated staphyloferrin into the cell. In this regard, the expression or function of at least one of the Hts polypeptides, e.g. HtsA, HtsB and HtsC, required for the transport of ferrated staphyloferrin A into the cell, and the expression or function of at least one of the Sir polypeptides, e.g. SirA, SirB and SirC, required for the transport of ferrated staphyloferrin B into the cell may be inhibited. Alternatively, expression of FhuC may be inhibited to inhibit the transport of both staphyloferrin A and staphyloferrin B into the cell.

As one of skill in the art will appreciate, staphyloferrin-mediated iron uptake may be inhibited by inhibiting the synthesis of staphyloferrin A and B (as set out above), the transport of staphyloferrin A and B into the cell (as set out above), as well as inhibiting the synthesis of staphyloferrin A combined with inhibiting the transport of staphyloferrin B into the cell, or inhibiting the transport of staphyloferrin A into the cell combined with inhibiting the synthesis of staphyloferrin B.

In order to identify agents that modulate staphyloferrin-mediated iron uptake, screening assays may be developed to screen for agents that modulate the iron-transport activity of the Sir or Hts polypeptides. For example, appropriate concentrations of test agents for modulating the iron-transport activity of the Hts proteins may be determined by any method known to one skilled in the art. In one embodiment, the screening assay may include whole *S. aureus* cells expressing wild type Hts and Sbt polypeptides. The ability of a compound to alter the iron transport activity of the Hts and/or Sbt polypeptides can be detected by analysis of the cells. For example, antagonists of iron-transport can by detected by scoring for alterations in growth or differentiation (phenotype) of the cell in iron-replete media. The growth of wild-type *S. aureus* strains in the presence of test agent(s) may be compared with the growth of SbtA, SbtB, SbtC, SbtD, HtsA, HtsB or HtsC deficient *S. aureus* strains. Each culture may be treated with a test agent from a library of compounds or natural extracts, and monitored for the effect that the particular agent has on the growth on the wild-type and the Hts-deficient strain. Bacterial growth may be monitored using a Klett meter. In this way, compounds that specifically interfere with the HtsABC/sbtABCD iron siderophore transport system can be identified.

As another example, *S. aureus* cells may be cultured and treated with test agents and then screened for the presence of iron in the cell using atomic absorption spectroscopy techniques. Alternatively, inhibition of the iron transport activity may be measured by using radioactively labeled iron. Compounds that interfere with the HtsABC iron siderophore transport system will result in a lowered uptake of the radioactively labeled iron. A control assay can also be performed to provide a baseline for comparison. In the control assay, the uptake of radioactively labeled iron in a *S. aureus* cell may be quantitated in the absence of the test compound. Examples of radioactively labeled iron may include $^{59}$Fe or $^{55}$Fe.

Antagonists that interfere with the expression of a nucleic acid or protein involved in siderophore-mediated iron uptake may also be identified. To identify such antagonists, *S. aureus* cells may be treated with a compound(s) of interest, and then assayed for the effect of the compound(s) on nucleic acid expression or protein production in respect of nucleic acids and corresponding encoded proteins involved in siderophore-mediated iron uptake. For example, total RNA can be isolated from *S. aureus* cells cultured in the presence or absence of test agents, using any suitable technique such as the single-step guanidinium-thiocyanate-phenol-chloroform method. The expression of nucleic acids such as sir, sbn, hts, sbt or fhu nucleic acids may then be assayed by any appropriate method such as Northern blot analysis, the polymerase chain reaction (PCR), reverse transcription in combination with the polymerase chain reaction (RT-PCR), and reverse transcription in combination with the ligase chain reaction (RT-LCR). Levels of mRNA encoding Sir, Sbn, Hts, Sbt or Fhu polypeptides may also be assayed, for example, using the RT-PCR method to determine the effect of a selected test agent in comparison to a control sample. The expression of Sir, Sbn, Hts, Stb or Fhu polypeptides may also be quantitated following the treatment of S. aureus cells with a test agent using antibody-based methods such as immunoassays. Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. For example, SbtA, SbtB, SbtC, SbtD, HtsA, HtsB or HtsC polypeptides may be detected in a sample obtained from S. aureus cells treated with a test agent, by means of a two-step sandwich assay. In the first step, a capture reagent (e.g., either a SbtA, SbtB, SbtC, SbtD, HtsA, HtsB or HtsC antibody) is used to capture the specific polypeptide. The capture reagent can optionally be immobilized on a solid phase. In the second step, a directly or indirectly labeled detection reagent is used to detect the captured marker. In one embodiment, the detection reagent is an antibody. The amount of SbtA, SbtB, SbtC, SbtD, HtsA, HtsB or HtsC polypeptide present in S. aureus cells treated with a test agent can be calculated by reference to the amount present in untreated S. aureus cells to determine the effect of the test agent on polypeptide expression.

Siderophore-mediated iron uptake by S. aureus may also be inhibited by interfering with the siderophore binding region within the Hts and Sir polypeptides, for example, the siderophore binding region within HtsA and SirA. As set out in the examples that follow, the binding region within these polypeptides has been identified and serves as a target region for inhibiting the interaction of Hts/Sir transport systems with ferrated siderophore for uptake. Thus, based on this determination of the binding region, antagonists can readily be designed to block Hts/Sir siderophore binding, and may include siderophore mimetics, immunological antagonists and the like.

Embodiments of the invention are described by reference to the following specific examples which are not to be construed as limiting.

EXAMPLES

Example 1

Materials and Methods for Examples 2 to 10

Bacterial Strains, Plasmids, and Growth Media.

Bacterial strains and plasmids used in this study are described in Table 1. Bacteria were cultured at 37° C., unless otherwise indicated.

TABLE 1

Bacterial strains, plasmids, and oligonucleotides used in this study

| Bacterial strains, plasmids, and oligonucleotides | Description[a] | Source or reference |
|---|---|---|
| Bacteria | | |
| E. coli | | |
| DH5α | Φ80dlacZΔM15 recA1 endA1 gyrA96 thi-1 hsdR17 ($r_K^-$ $m_K^+$) supE44 relA1 deoR Δ(lacZYA-argF)U169 | Promega |
| ER2566 | F[-] λ[-] fhuA2 [lon] ompT lacZ::T7 geneI gal sulA11 Δ(mcrC-mrr)114::IS10 R(mcr-73::miniTn10)2 R(zgb-210::Tn10)1 (Tet[S]) endA1 [dcm] | New England Biolabs |
| RP523 | thr-1 leuB6 thi-1 lacY1 tonA21 supE44 F[-] λ[-] hemB | (Li et al., 1988) |
| S. aureus | | |
| RN4220 | $r_K^-$ $m_K^+$; accepts foreign DNA | (Kreiswirth et al., 1983) |
| RN6390 | Prophage-cured wild type strain | (Peng et al., 1988) |
| Newman | Wild type clinical isolate | (Duthie and Lorenz, 1952) |
| H1324 | RN6390 ΔsbnABCDEFGHI::Tet; Tet[R] | This study |
| H1331 | Newman ΔsbnABCDEFGHI::Tet; Tet[R] | This study |
| H1661 | RN6390 ΔsbtABCD::Km; Km[R] | This study |
| H1665 | Newman ΔsbtABCD::Km; Km[R] | This study |
| H1649 | RN6390 ΔsbnABCDEFGHI::Tet ΔsbtABCD::Km; Tet[R] Km[R] | This study |
| H1666 | Newman ΔsbnABCDEFGHI::Tet ΔsbtABCD::Km; Tet[R] Km[R] | This study |
| H306 | RN6390 sirA::Km; Km[R] | (Dale et al., 2004b) |
| H803 | Newman sirA::Km; Km[R] | (Dale et al., 2004b) |

TABLE 1-continued

Bacterial strains, plasmids, and oligonucleotides used in this study

| | | |
|---|---|---|
| H1448 | RN6390 ΔhtsABC::Tet; Tet$^R$ | This study |
| H1262 | Newman ΔhtsABC::Tet; Tet$^R$ | This study |
| H1480 | RN6390 sirA::Km ΔhtsABC::Tet; Tet$^R$ Km$^R$ | This study |
| H1497 | Newman sirA::Km ΔhtsABC::Tet; Tet$^R$ Km$^R$ | This study |
| H706 | Newman fur::Km; Km$^R$ | (Dale et al., 2004b) |
| *S. epidermidis* | | |
| 846-1 | Plasmid-cured type strain | W. Kloos |
| 1457-M10 | Biofilm deficient (ica$^-$) mutant; Em$^R$ | (Dobinsky et al., 2002) |
| *S. saprophyticus* ATCC 15305 | Clinical type strain | (Kuroda et al., 2005) |
| Plasmids | | |
| pAUL-A | Temperature-sensitive *S. aureus* suicide vector; Em$^R$ Lc$^R$ | (Chakraborty et al., 1992) |
| pALC2073 | *E. coli/S. aureus* shuttle vector; Am$^R$ Cm$^R$ | (Bateman et al., 2001) |
| pBAD30-IsdE | pBAD30 derivative encoding the IsdE protein; Ap$^R$ | (Muryoi et al., 2008) |
| pBC SK(+) | *E. coli* cloning vector; Cm$^R$ | Stratagene |
| pDG780 | BluescriptKS$^+$ derivative that carries a kanamycin resistance cassette; Ap$^R$ | (Guérout-Fleury et al., 1995) |
| pDG1513 | pMTL22 derivative that carries a tetracycline resistance cassette; Ap$^R$ | (Guérout-Fleury et al., 1995) |
| pET28a(+) | Vector for overexpression of His-tagged proteins using the T7 bacteriophage promoter; Km$^R$ | Novagen |
| pEV55 | pLI50 derivative containing htsABC from *S. aureus*; Cm$^R$ | This study |
| pEV83 | pAUL-A derivative containing htsABC::Tet; Em$^R$ Tet$^R$ | This study |
| pEV90 | pLI50 derivative containing sbtABCD from *S. aureus*; Cm$^R$ | This study |
| pEV93 | pLI50 derivative containing htsABC from *S. epidermidis*; Cm$^R$ | This study |
| pEV95 | pLI50 derivative containing sbtABCD from *S. epidermidis*; Cm$^R$ | This study |
| pEV96 | pLI50 derivative containing sbtABCD from *S. saprophyticus*; Cm$^R$ | This study |
| pEV98 | pET28a(+) derivative encoding soluble portion of protein SirA; Km$^R$ | This study |
| pEV99 | pET28a(+) derivative encoding the soluble portion of protein HtsA; Km$^R$ | This study |
| pFB10 | pAUL-A derivative containing ΔsbnABCDEFGHI::Tet; Em$^R$ Tet$^R$ | This study |
| pFB24 | pXEN-1 derivative containing P$_{sbtA}$ | This study |
| pFB25 | pXEN-1 derivative containing P$_{sbtBCD}$ | This study |
| pFB26 | pXEN-1 derivative containing P$_{htsABC}$ | This study |
| pFB50 | pLI50 derivative with repB frameshift mutation, containing ΔsbtABCD::Km; Cm$^R$ Km$^R$ | This study |

TABLE 1-continued

Bacterial strains, plasmids, and oligonucleotides used in this study

| | | |
|---|---|---|
| pFB54 | pALC2073 tetO/R⁻ derivative containing a transcriptional fusion of *S. aureus* fhuC and sirABC operons | This study |
| pFB56 | pALC2073 tetO/R⁻ derivative containing the *S. aureus* fhuC gene | This study |
| pFB55 | pALC2073 tetO/R⁻ derivative containing a transcriptional fusion of *S. aureus* fhuC and sirABC operons, where fhuC has a 3' end deletion | This study |
| pLI50 | *E. coli/S. aureus* shuttle vector; $Ap^R$ $Cm^R$ | (Lee and landolo, 1986) |
| psirABC | pBC SK(+) derivative containing sirABC | (Dale et al., 2004b) |
| pUC 19 | *E. coli* cloning vector; $Ap^R$ | (Yanisch-Perron et al., 1985) |

| Oligonucleotides[b] Purpose | Sequence |
|---|---|
| Cloning of sbtAsbtBCD from *S. aureus* | GTATAGATTGTATTTAATAAGTTAATGTAATCC (forward)<br>TGCAAACGATATGTAGTATAACTTGTCAAC (reverse) |
| Cloning of sbtAsbtBCD from *S. epidermidis* | ATAT<u>GAATTC</u>TTGAGCATGACGCTCAAGTGC (forward, EcoRI)<br>ATAT<u>CCCGGG</u>GAGACGGTGCGTTGAGTTAAAGG (reverse, SmaI) |
| Cloning of htsABC from *S. aureus* | T<u>GAGCTC</u>TGCGATTACATTGGAGGCTG (forward, SacI)<br>TG<u>CCCGGG</u>GTTAGTTATTTCATTCTTCG (reverse, SmaI) |
| Cloning of htsABC from *S. epidermidis* | CAGT<u>TCTAGA</u>CCTTGTTCAGAACTTCGATATG (forward, XbaI)<br>CAGT<u>GAGCTC</u>CAGGCTCTATAACTAAAAAATACG (reverse, SacI) |
| Cloning of fhuC from *S. aureus* | TTGATA<u>GCATGC</u>CATGACAAATCGAGCTATCC (forward, SphI)<br>TTGATA<u>CTGCAG</u>TTAAGAATAAGCTCTGCGACA (reverse, PstI) |
| Cloning of sbtA promoter from *S. aureus* | TTGCGC<u>GAATTC</u>CATAAAACTTACACCCGCATTC (forward, EcoRI)<br>TTGCGCGGATCCCATAATTCACCTCTATGAAATA (reverse, BamHI) |
| Cloning of sirA (soluble component) from *S. aureus* | AA<u>CATATG</u>ACAACTTCAATTAAACATGCAATG (forward, NdeI)<br>AA<u>GAATTC</u>CTCCTTAATTATTTTGATTGTTTTC (reverse, EcoRI) |
| Cloning of htsA (soluble component) from *S. aureus* | AA<u>GCTAGC</u>ACTATTTCGGTAAAAGATGAAAATG (forward, NheI)<br>AA<u>GGATCC</u>CATTTACTTCCACCTTACTTTTGTTC (reverse, BamHI) |
| RT-PCR: sbtA | CCTCTAATGCAATGCCATATTTA (forward)<br>ACAATGAATCACCTATCGTGACA (reverse) |
| RT-PCR: sbtB | AGTCTATCATGCGCCAACAAC (forward)<br>AACCTGTCGCCATAATCAATAA (reverse) |
| RT-PCR: htsA | TTTAAATCCAGAGCGTATGATCA (forward)<br>CAGAAGAAATTAAGCCACGAGAT (reverse) |
| RT-PCR: gyrB | ATAATTATGGTGCTGGGCAAAT (forward)<br>AACCAGCTAATGCTTCATCGATA (reverse) |

[a]Abbreviations: $Ap^R$, $Cm^R$, $Em^R$, $Km^R$, $Lc^R$, and $Tet^R$, resistance to ampicillin, chloramphenicol, erythromycin, kanamycin, lincomycin, and tetracycline, respectively; ATCC, American Type Culture Collection.,
[b]Restriction sites for cloning of PCR products are underlined.

Antibiotics were used at the following concentrations: ampicillin (100 µg/mL) and erythromycin (300 µg/mL) for *E. coli* selection; chloramphenicol (5 µg/mL), tetracycline (10 µg/mL), kanamycin (50 µg/mL), neomycin (50 µg/mL), and erythromycin (3 µg/mL) for *S. aureus* selection. For molecular-genetic manipulations, bacteria were grown in Luria-Bertani (for *E. coli*) or tryptic soy broth (for *S. aureus*). Iron restricted media were either i) the chemically-defined Tris-minimal succinate medium {Sebulsky, 2004 #1227} containing 0.1 µM ethylenediamine-di-o-hydroxyphenylacetic acid (LGC Promochem), ii) RPMI broth (Gibco BRL) containing 1% w/v casamino acids (Difco), or iii) a 60:40 ratio of complement-inactivated horse serum (Sigma-Aldrich) to TMS broth. All solutions and media were made with water purified through a Milli Q water purification system (Millipore).

Recombinant DNA Methodology.

Plasmid DNA was isolated from bacteria using Qiaprep mini-spin kits (Qiagen), as directed. For plasmid isolation from *S. aureus*, cells were incubated for 30 min at 37° C. in P1 buffer containing 50 mg/mL lysostaphin (Roche Diagnostics) prior to addition of lysis buffer P2. Restriction endonucleases, T4 DNA ligase, Klenow fragment, and PwoI polymerase were obtained from Roche Diagnostics, and oligonucleotides were purchased from Integrated DNA Technologies.

sbn Operon Deletion.

The sbnABCDEFGHI::Tet knockout allele consisted of the tetracycline resistance cassette, excised from plasmid pDG1513 with restriction enzymes SspI and NaeI and blunted with Klenow enzyme, flanked by DNA sequences homologous to regions upstream of sbnA and immediately downstream of sbnI. The knockout allele was cloned to the temperature sensitive *E. coli/S. aureus* shuttle vector pAUL-A, and subsequently passaged through *S. aureus* RN4220 prior to transduction into *S. aureus* RN6390. Recombinant RN6390 was cultured at 30° C. to mid-log phase before the incubation temperature was shifted to 42° C. and bacteria were incubated a further 16 hours before being plated onto TSA containing tetracycline. Colonies were screened for sensitivity to erythromycin, indicating a loss of pAUL-A backbone DNA following integration of the knockout allele into the chromosome via homologous recombination on either side of the tetracycline resistance cassette. The sbn::tet deletion was mobilized to other *S. aureus* backgrounds by transduction using phage 80α.

sbt Locus Deletion.

The sbtABCD::Kan knockout allele consisted of the kanamycin resistance cassette, excised from plasmid pDG780 flanked by DNA sequences homologous to regions downstream of sbtA and sbtD, and cloned into the *E. coli/S. aureus* shuttle vector pLI50. A *S. aureus* suicide vector was generated from this plasmid by introduction of a frameshift mutation into repB (encoding the Gram-positive replicase protein) following NsiI digestion and Klenow fragment fill-in. This plasmid, incapable of unassisted replication in *S. aureus*, was introduced into *S. aureus* strain RN4220 carrying unmodified pLI50, enabling replication through complementation in trans with wild type RepB. The construct was then transduced to *S. aureus* strain RN6390 and recombinant bacteria were plated onto TSA containing kanamycin and neomycin. Colonies were screened for sensitivity to chloramphenicol, indicating a loss of vector DNA following homologous recombination on either side of the kanamycin resistance gene. The sbt::kan deletion was mobilized to other *S. aureus* backgrounds by transduction using phage 80α.

htsABC::Tet Deletion.

The htsABC::Tet knockout allele targeted the 5' and 3' noncoding regions around htsABC. The 5' arm was PCR amplified and cloned SacI to BamHI to plasmid pUC19, followed by PCR amplified 3' arm cloned BamHI to XbaI. A tetracycline resistance cassette was excised from plasmid pDG1513 with restriction enzymes BamHI and BglII and cloned into the arms at the SmaI site. The knockout allele was excised and cloned to shuttle vector pAUL-A, SadI to XbaI. Passaging to *S. aureus* and selection for chromosomal integration was performed as described for the sbn operon mutation.

Complementation Vectors.

The *S. aureus* sbtAsbtBCD::Km mutant was complemented using plasmid pEV90. Additionally, complementation was performed using sbtAsbtBCD from *S. epidermidis* 846-1 and *S. saprophyticus* ATCC 15305. These loci were PCR amplified and cloned to pLI50 between restriction sites EcoRI and SmaI (*S. epidermidis*) or BamHI and SmaI (*S. saprophyticus*). htsABC::Tet mutants were complemented using plasmids pEV55 and pEV93. hts operons was PCR amplified from *S. aureus* Newman (pEV55) or *S. epidermidis* 846-1 (pEV93) and cloned to pLI50 between restriction sites SacI and SmaI or SacI and XbaI, respectively. Vectors were constructed in *E. coli* DH5α, electroporated into *S. aureus* strain RN4220, and transduced to *S. aureus* RN6390 and Newman strain lines using phage 80α.

Growth Curves.

Bacteria were cultured for 12 hours in TMS broth then 12 hours in TMS broth containing 100 µM 2,2' dipyridyl (Sigma). Cells were washed twice in saline, and diluted 1:100 into 60% horse serum/40% TMS broth. For iron replete media, 50 µM $FeCl_3$ was included. Cultures were grown under constant medium amplitude shaking in a Bioscreen C machine (Growth Curves, USA). Optical density was measured at 600 nm every 30 min.

Supernatant Preparations and Plate Bioassays.

*S. aureus* strains were grown with aeration in TMS broth containing 0.1 µM EDDHA for 40 h at 37° C. Cells were removed by centrifugation and supernatants were lyophilized. Dried supernatant was extracted with methanol (half the original supernatant volume), passed through Whatman no. 1 filter paper to remove insoluble material, and rotary evaporated. Material was solubilized in water to 5% of the original supernatant volume. The ability of supernatant concentrates to promote the iron-restricted growth of *S. aureus* was assessed using siderophore plate bioassays, performed as previously described (Sebulsky et al., 2000) with modifications. Briefly, *S. aureus* strains were incorporated into TMS agar ($1 \times 10^4$ cells/ml) containing 7.5 µM EDDHA. Concentrates (10 µL) were added to sterile paper discs which were then placed onto the plates. Growth promotion was quantified by measuring the radius of growth around the disc after 36 hours at 37° C.

Example 2

*S. aureus* sbn Mutants Still Produce Siderophore

Strains of *S. aureus* containing complete sbn operon deletions (i.e. deleted for all of sbnA through sbnI genes) were constructed. In *S. aureus* Newman background, the sbn deletion strain was called H1331 whereas in RN6390 background, it was called H1324. When cultured in serum at 37°

Figure 2:
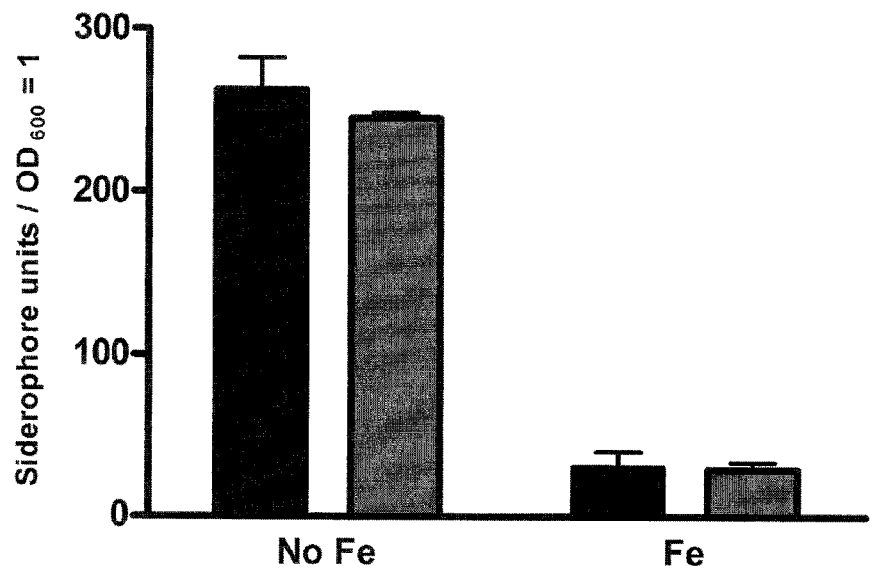
FIG. 2 is a bar graph comparing siderophore production in wild-type *S. aureus* (black bars) with an *S. aureus* sbn operon deletion strain (grey bars) in the presence and absence of iron.

C., H1331 demonstrated markedly impaired growth during the first 15 hours of incubation compared to wildtype Newman, before eventually growing to an equivalent cell density as Newman by approximately 30 hours (FIG. 1). Analysis of the spent culture supernatant, from the 35 h timepoint, for iron chelating activity using the chrome azurol S assay (Schwyn and Neilands, 1987) revealed comparable siderophore activity between Newman and H1331 (FIG. 2). Supplementation of serum growth media with iron obviated the growth defect of H1331 (FIG. 1, inset), and suppressed siderophore production in both Newman and H1331 (FIG. 2). Finally, concentrated supernatant from both *S. aureus* Newman and H1331, both cultured in iron-restricted TMS media, promoted growth of *S. aureus* (Newman and RN6390 responded equivalently) in siderophore plate bioassays (Table 2). To ensure that this was not due to a strain-specific phenomenon, all experiments described above were repeated using instead the RN6390 genetic background (i.e. RN6390 vs. H1324). Equivalent results were obtained (data not shown).

TABLE 2

S. aureus supernatants promote growth of wildtype S. aureus Newman

| Concentrated supernatant | Growth promotion of strain Newman[a] |
|---|---|
| Newman | 12.17 ± 0.29[b] |
| H1331 (Newman Δsbn) | 8.17 ± 0.58 |
| H1665 (Newman Δsbt) | 11.83 ± 0.29 |
| H1666 (Newman Δsbn Δsbt) | 0 |

[a]Growth promotion of supernatants on strain RN6390 was equivalent to that observed for strain Newman;
[b]Growth promotion is measured as the diameter of growth around disc.

Taken together, these findings indicate that *S. aureus* synthesizes at least two siderophores, one of which does not require any of the products of the sbn operon for synthesis. The production of this additional siderophore compensates for the absence of the sbn-derived siderophore (staphylobactin/staphyloferrin B), but only after prolonged incubation in serum.

Example 3

Figure 3:
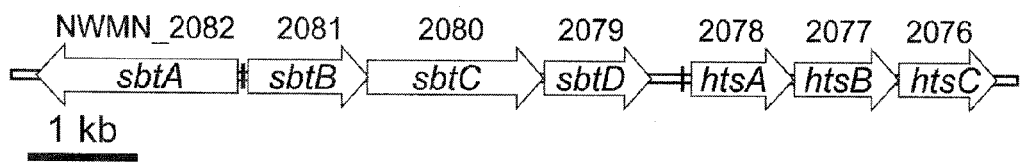
FIG. 3 is a schematic representation of the sbt-hts region of the *S. aureus* chromosome including locus numbers from the sequenced chromosome of strain Newman.

A Second Iron-Regulated Siderophore Biosynthetic Locus in *S. aureus* is Also Conserved Among Coagulase-Negative Staphylococci Since *S. aureus* sbn deletion mutants still produced siderophore, other genetic loci in *S. aureus* whose products would be capable of synthesizing a siderophore were determined. Examination of the available *S. aureus* genome sequences identified a four-gene locus with potential to encode siderophore biosynthetic enzymes; in strain Newman, these open reading frames are identified as NWMN_2079-NWMN_2082 (FIG. 3). This locus was identified as sbt, for siderophore biosynthesis two. The sbt locus resides on the genome immediately upstream of the htsABC operon (NWMN_2078-2076), encoding components of an ABC transporter that was previously proposed to transport heme into the staphylococcal cell. sbtA is divergently transcribed from what is likely a polycistronic message comprised of sbtB-sbtD.

In contrast to the sbn operon which, among the staphylococci, is only present in *S. aureus* species, the sbt locus is conserved in coagulase-negative staphylococci, at least where genomic information is available. As shown in Table 3, predicted Sbt products share significant similarity with predicted protein products from *S. epidermidis*, *S. haemolyticus* and *S. saprophyticus* indicating the functional similarity among these *Staphylococcal* Sbt products.

TABLE 3

The sbt locus is found in S. aureus as well as CoNS

| S. aureus protein | Percent identity; total similarity | | |
|---|---|---|---|
| | S. epidermidis | S. haemolyticus | S. saprophyticus |
| SbtA | 59; 71 | 54; 64 | 53; 64 |
| SbtB | 71; 84 | 64; 80 | 60; 75 |
| SbtC | 64; 74 | 58; 71 | 59; 72 |
| SbtD | 62; 76 | 56; 70 | 58; 74 |

Figure 5:
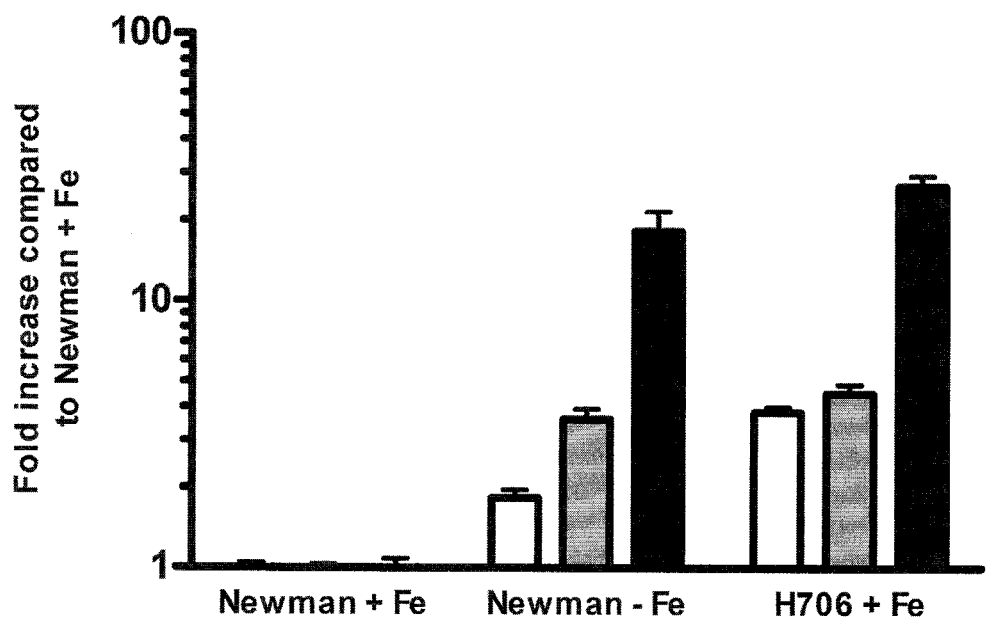
FIG. 5 is a bar graph showing that transcription of the sbt-hts locus, namely sbtA (white bars), sbtB (grey bars), and htsA (black bars), is regulated by iron and Fur.

The intergenic region between divergently oriented sbtA and sbtB genes, and the region immediately upstream of the htsABC operon contain 19-bp sequences (see FIGS. 3 and 4) that are highly similar to consensus Fur box sequences, suggesting that the sbtA, sbtB, and hts transcripts are iron-regulated via the activity of the ferric uptake regulator (Fur) repressor protein. Consistent with the observation that siderophore is only made by *S. aureus* during iron restriction (FIG. 2), and similar to the regulation observed for the sbn operon, both the sbtA and sbtB transcripts were up-regulated in an iron and Fur-dependent manner (FIG. 5). The htsABC operon was shown to be regulated in a similar fashion (FIG. 5).

Example 4

Figure 6:
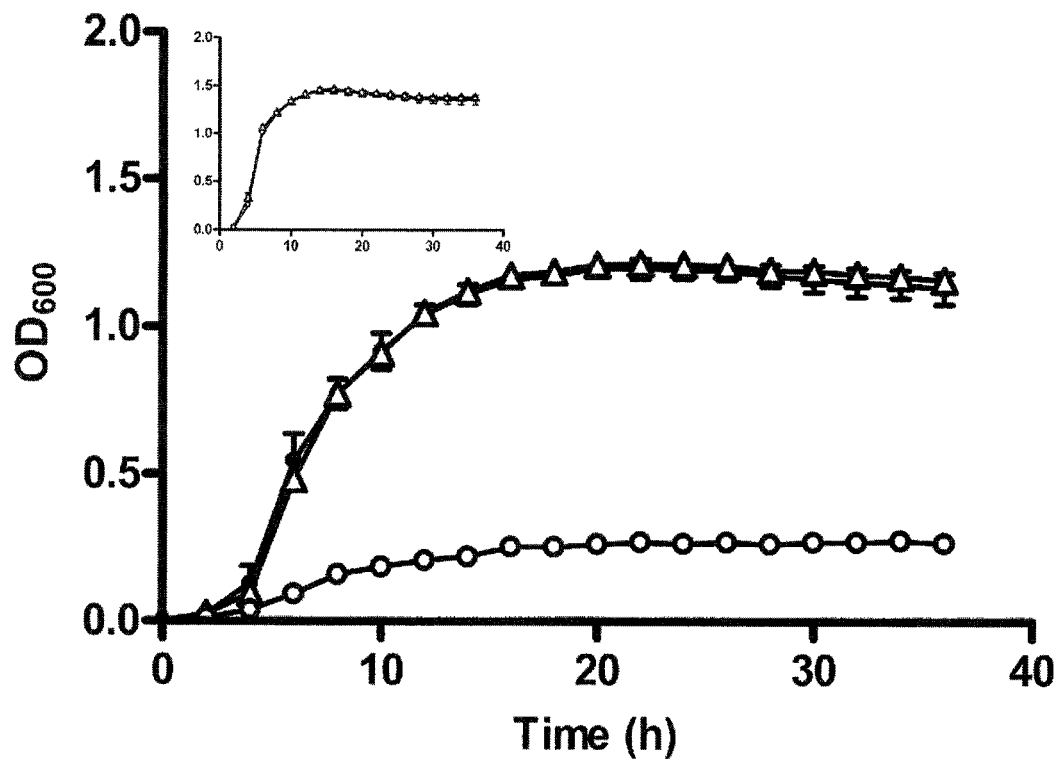
FIG. 6 graphically compares the growth of wild-type *S. aureus* (●), an *S. aureus* sbt operon deletion strain (ΔsbtAB-CD::Tet) (Δ) and an *S. aureus* tandem sbn/sbt locus mutant (ΔsbnABCDEFGHI::Tet ΔsbtABCD::Kan) (○) in serum, and the inset graphically illustrates growth of the tandem deletion strain in serum supplemented with $FeCl_3$.
Figure 7:
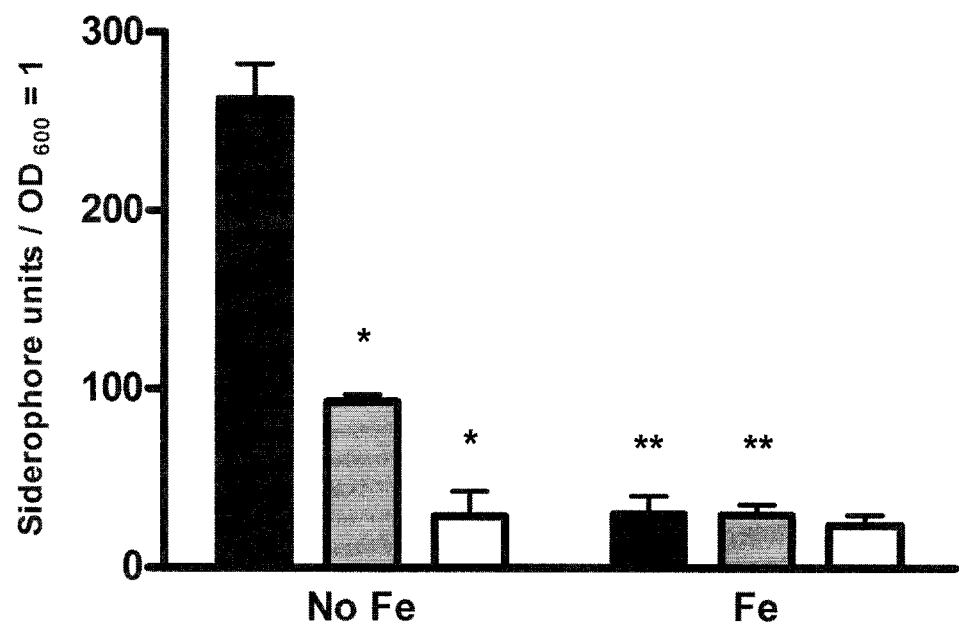
FIG. 7 is a bar graph comparing siderophore production in wild-type *S. aureus* (black bars) with an *S. aureus* sbt operon deletion strain (grey bars) and an *S. aureus* tandem sbn/sbt locus mutant (white bars) in the presence and absence of iron.

Deletion of the sbt Locus in Wildtype *S. aureus* Backgrounds Yields No Growth-Deficient Phenotype, but does have an Additive Affect on Growth when Combined with sbn Locus Deletion As described above, the sbt genes are expressed under conditions of iron limitation, and two of the genes (sbtA and sbtC) encode products with similarity to siderophore biosynthesis enzymes. It was, thus, hypothesized that deletion of the locus would lead to a drop in siderophore production, and consequently this would result in a strain deficient in its ability to grow in iron-restricted growth media (e.g. serum), mimicking what was observed for strains harboring sbn operon deletions (see FIG. 1). Strain H1665, which is strain Newman carrying a deletion of the sbtABCD gene cluster, was created. Surprisingly, it was found that, in contrast to strain H1331 (sbn locus deletion), there was no discernible growth attenuation in strain H1665 in serum (FIG. 6), in spite of the fact that endpoint analysis of culture supernatants identified a significant decrease in siderophore output compared with wildtype (FIG. 7). Concentrated culture supernatant from H1665 was able to readily promote the growth of iron-restricted wildtype *S. aureus* strains (Table 2), indicating the presence of at least one siderophore molecule (likely encoded by products of at least the sbn genes).

To address whether Sbn-mediated siderophore activity was able to compensate for the loss of Sbt-mediated siderophore activity, both deletions were combined into one strain, H1666. Compared with either strain H1331 (Δsbn) or H1665 (Δsbt), strain H1666 (Δsbn Δsbt) demonstrated severe attenuation of growth in serum (FIG. 6). Growth of H1666 could, however, be resuscitated to wildtype levels if the growth media were replete with iron (FIG. 6, inset), indicating that the growth deficiency is due solely to the inability to scavenge available iron. Endpoint analysis of iron-restricted supernatants of the H1666 revealed that siderophore activity was reduced to background levels (FIG. 7). Importantly, concentrated culture supernatant from iron-restricted H1666 did not contain any molecule capable of promoting the iron-restricted growth of wildtype S. aureus (Table 2).

Taken together, these data strongly suggest that all siderophore production by S. aureus is mediated by the sbn and sbt loci in the production of independent siderophores. To rule out potential strain specific effects, all deletions were reconstructed in the RN6390 background, and similar growth and siderophore activity trends were observed (data not shown).

Example 5

The sirABC and htsABC Operons Encode ABC Transporters Associated with Transport of the sbn-Derived Siderophore and the sbt-Derived Siderophore, Respectively The transport of staphylobactin, produced by enzymes encoded within the sbn operon, is mediated by the SirABC ABC transporter (Dale et al., 2004a; Dale et al., 2004b, the contents of which are incorporated herein), which is encoded from an operon divergently transcribed from the sbn operon.

Figure 8:
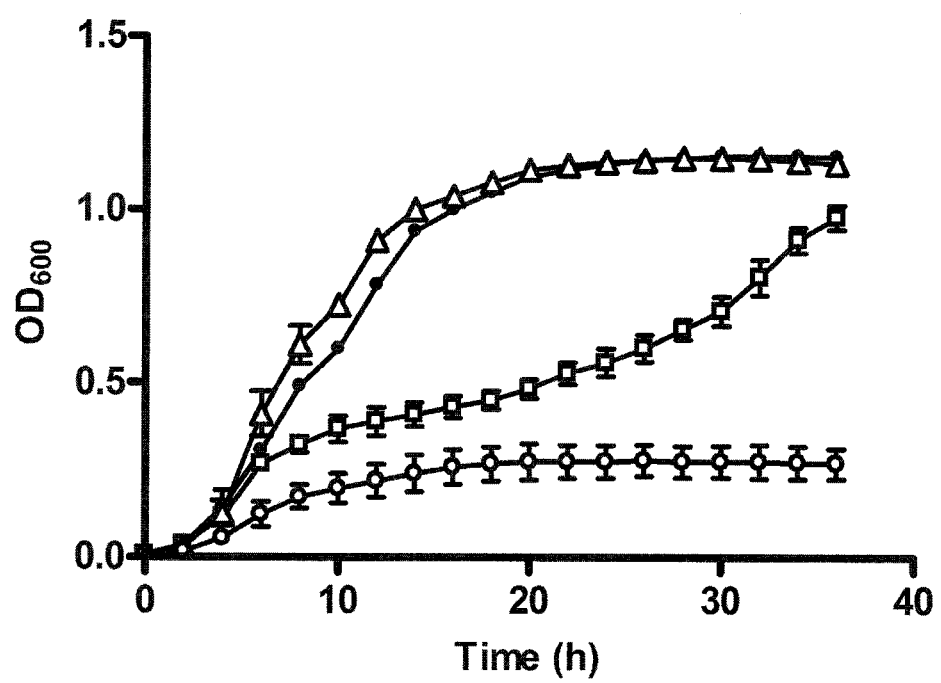
FIG. 8 graphically illustrates the effect of ABC transporter gene inactivations on the growth of *S. aureus* wild-type (●), sirA::Km (□), ΔhtsABC (Δ), and tandem sirA/htsABC (○)

The relationship between the htsABC operon and the sbt locus (see FIG. 3), was then determined, despite the previous suggestion that HtsABC was involved in heme transport. Initially, it was noted that the growth kinetics, in serum, of H803 (sirA::Km) were very similar to those observed for H1331 (Δsbn) (FIG. 8). Similar to the lack of a growth defect in serum for H1665 (Δsbt), there was no growth defect for the htsABC deletion strain, H1262 (FIG. 8). Also similar to the results observed for mutants containing the double siderophore biosynthetic loci deletions (H1666 (Δsbn Δsbt)), inactivation of sirA and htsABC in the same strain (H1497) lead to drastic growth attenuation in serum (FIG. 8). More direct evidence for the role of HtsABC in transport of siderophore derived from the function of sbt gene products was obtained through siderophore plate bioassays. Spent culture supernatants from each of H1331, H1665 and H1666 grown under iron-restricted conditions were concentrated and provided to wildtype, sirA::Km, ΔhtsABC and sirA::Km ΔhtsABC strains. As shown in Table 4, material produced by wildtype cells could promote growth of all strains except the double sirA::KmΔhtsABC mutant, whereas material derived from H1331 (Δsbn) could only promote growth of wildtype and sirA::Km cells, and material derived from H1665 (Δsbt) could only promote growth of wildtype and htsABC::erm cells. Last, concentrated spent culture supernatant from H1666 was unable to promote growth of any S. aureus strain, including wildtype S. aureus (see also Table 2). This indicates that the sbn and sbt genes produce distinct material or siderophore with a non-overlapping specificity for their respective SirABC and HtsABC transport system.

TABLE 4

| Concentrated supernatant | Strain | | | |
|---|---|---|---|---|
| | Newman | H803 (Newman ΔsirA) | H1262 (Newman ΔhtsABC) | H1497 (Newman ΔsirA ΔhtsABC) |
| WT | 12.17 ± 0.29[a] | 8.33 ± 0.29 | 13.17 ± 0.29 | 0.00 |
| Δsbt | 11.83 ± 0.29 | 0.00 | 13.83 ± 0.29 | 0.00 |
| Δsbn Δsbt | 0.00 | 0.00 | 0.00 | 0.00 |
| Δsbt pEV90 | 11.83 ± 0.29 | 10.17 ± 0.29 | 10.83 ± 0.29 | 0.00 |

TABLE 4-continued

| Concentrated supernatant | Strain | | | |
|---|---|---|---|---|
| | Newman | H803 (Newman ΔsirA) | H1262 (Newman ΔhtsABC) | H1497 (Newman ΔsirA ΔhtsABC) |
| Δsbn Δsbt pEV90 | 11.33 ± 0.29 | 12.17 ± 0.29 | 0.00 | 0.00 |
| Δsbt pEV95 | 12.33 ± 0.29 | 10.17 ± 0.29 | 12.17 ± 0.29 | 0.00 |
| Δsbn Δsbt pEV95 | 10.67 ± 0.29 | 10.83 ± 0.29 | 0.00 | 0.00 |

[a]Growth promotion is measured as the diameter of growth around disc. See Materials and Methods for assay details.

Example 6 sbtABCD and htsABC from S. epidermidis Complement S. aureus Mutants

Figure 9:
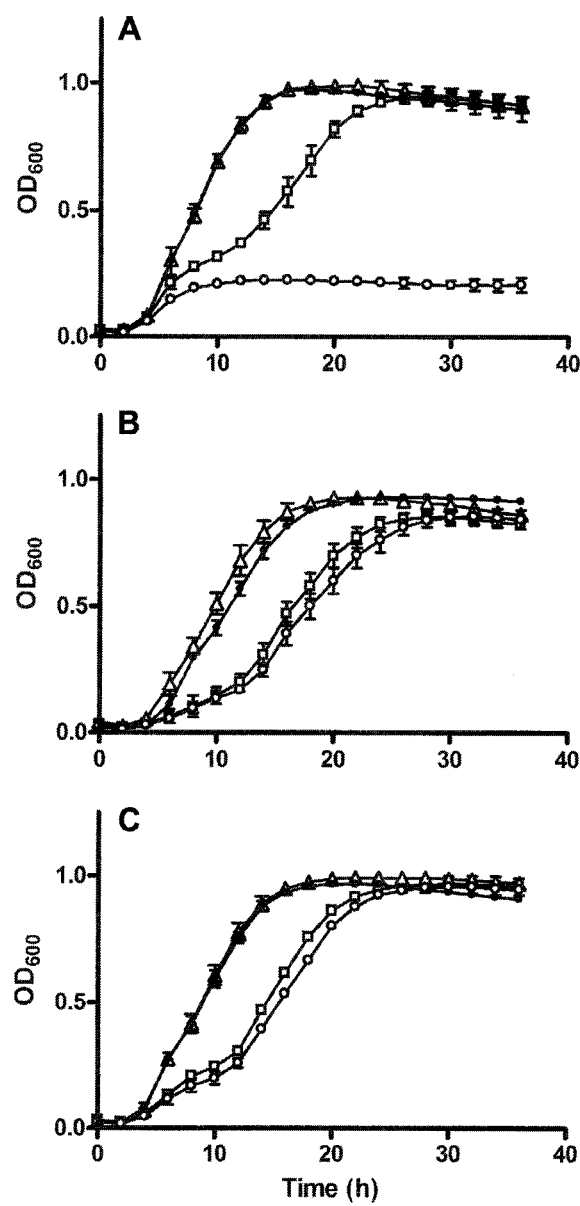
FIG. 9 graphically illustrates the growth in serum of *S. aureus* wild-type (●), ΔsbnABCDEFGHI::Tet (□), ΔsbtAB-CD::Km (Δ) and tandem Δsbn/Δsbt (○) transformed with empty cloning vector (pLI50) (A), a plasmid carrying sbtABCD from *S. aureus* (pEV90) (B) and a plasmid carrying sbtABCD from *S. epidermidis* (pEV95) (C)

As stated above, in contrast to sirABC and sbnA-I which, among the staphylococci are only found in S. aureus, genome sequences from coagulase-negative staphylococci (CoNS) contain homologs of sbtABCD (see Table 4). To determine whether CoNS sbt homologs are functionally analogous to those in S. aureus, it was determined whether the S. epidermidis sbt genes would complement the S. aureus sbt growth defect and, secondly, whether a product would be made that could be transported through S. aureus HtsABC. As shown in FIG. 9, growth in serum of the siderophore-deficient S. aureus mutant H1666 (i.e. Δsbn Δsbt) was capable of being equivalently augmented when containing the sbt locus either from S. aureus or S. epidermidis. Interestingly, the multicopy sbt genes were incapable of promoting faster growth of H1331 (i.e. Δsbn). Evidence that the sbt genes from S. epidermidis synthesize an identical (or highly similar) molecule as that produced by sbt genes from S. aureus is derived from the result that sbt genes in trans, whether from S. aureus or S. epidermidis, in H1666 (i.e. Δsbn Δsbt) produced culture supernatant capable of promoting growth of wildtype S. aureus and S. aureus ΔsirA, but not ΔhtsABC mutants of S. aureus.

Example 7

Lack of Evidence for Heme Binding or Transport by S. aureus Hts

A previous report indicated that mariner transposon insertion into hts lead to a strain that preferentially took iron from transferrin, as opposed to heme, leading to the suggestion that htsABC encoded an ABC transporter specific for heme. However, evidence is provided herein that S. aureus HtsABC is involved in transport of a siderophore molecule that is made by the products of the sbt locus, a locus that is transcribed from the chromosome directly upstream of htsABC. In this example, direct evidence for heme transport by HtsABC or, at the very least, heme binding by the solute binding protein, HtsA, was tested.

Figure 10:
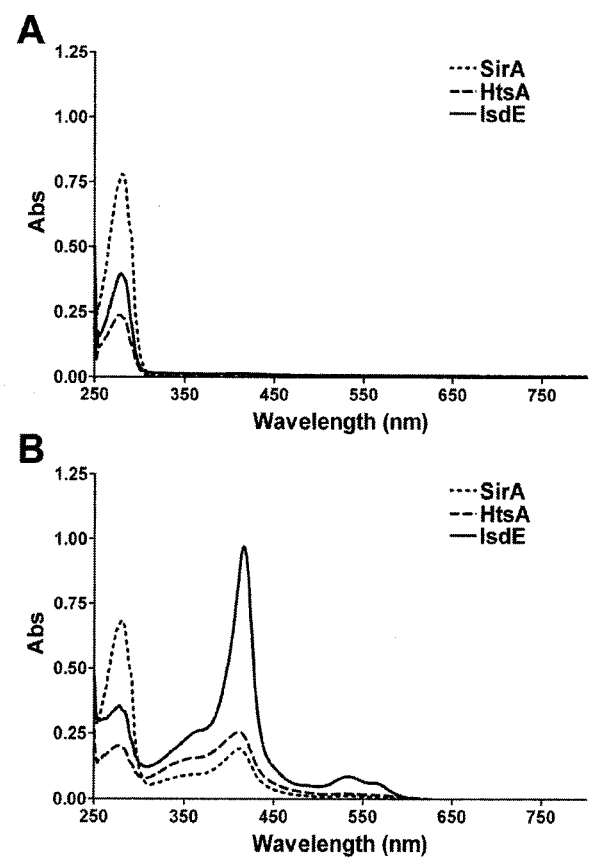
FIG. 10 illustrates the absorption spectra of purified IsdE, HtsA and SirA proteins in the absence of heme (A) and on exposure to heme (B)

In liquid growth assays, no attenuation of the htsABC deletion mutant, H1665, when grown on heme as a sole iron source (data not shown) was observed. Moreover, as shown in FIG. 10, when assayed for heme binding functionality, little to no heme would associate with purified HtsA in comparison to IsdE, a lipoprotein proven to associate with heme. This indicates that, in contrast to what was previously thought, Hts is involved in the transport of siderophore-bound iron, as opposed to heme.

Example 8

Several *S. aureus* Sbn Mutants Demonstrate an Iron-Restricted Growth Defect

A nine-gene operon called sbn for siderophore biosynthesis, has been identified. In order to determine if sbn products play a role in siderophore production, Δsbn *S. aureus* mutants, including sbnA, sbnB, sbnC, sbnD, sbnE, sbnF and sbnH have been generated. Growth assays with each of these mutants has shown that none of these mutants make staphylobactin and all of these mutants grow poorly in iron-restricted media such as in human or animal sera. Therefore, at least sbnA, sbnB, sbnC, sbnD, sbnE, sbnF, sbnH or their respective encoded protein products are candidate targets for inhibitors of staphylobactin biosynthesis. Thus, sbn nucleic acids, corresponding encoded Sbn protein products or corresponding *S. aureus* Sbn mutants can be used in screening methods to identify inhibitors of the staphylobactin biosynthetic pathway. Furthermore, components of reactions catalyzed by Sbn enzymes, as well as the Sbn enzymes themselves, may be used to develop biochemical assays for use in high-throughput screening for inhibitors of Sbn enzymes.

Example 9

Biochemical Assays Using SbnA and SbnB

Figure 11:
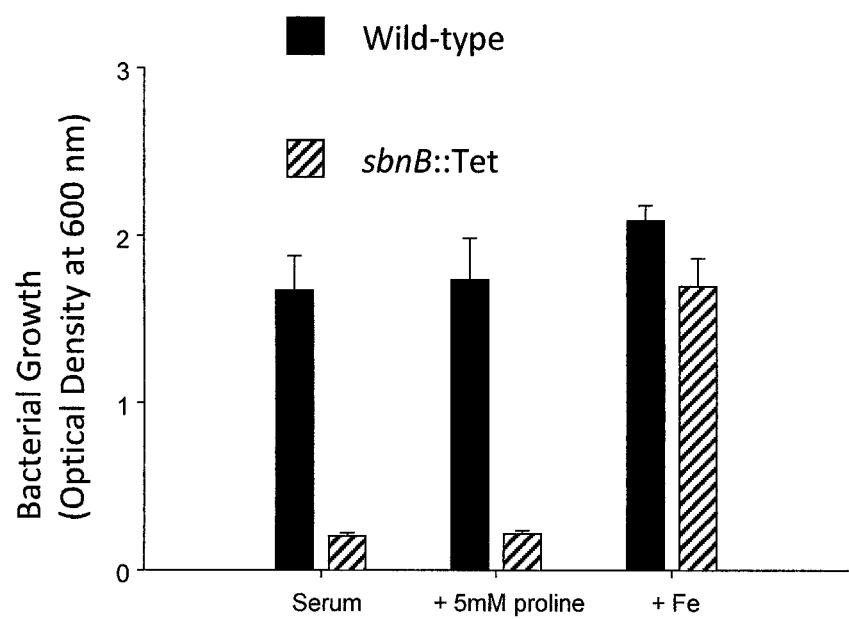
FIG. 11 is a bar graph comparing bacterial growth of *S. aureus* wild-type and an sbnB mutant in the absence and presence of proline and iron.
Figure 12:
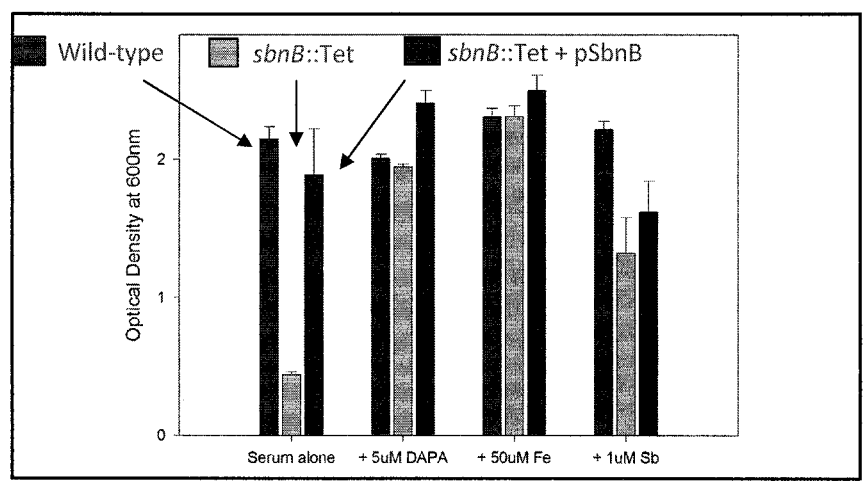
FIG. 12 is a bar graph comparing bacterial growth of *S. aureus* wild-type, an sbnB mutant and an sbnB mutant including a plasmid carrying sbnB in the absence and presence diaminopropionic acid (DAPA), Fe and Sb.

As mentioned in Example 8 several dsbn *S. aureus* mutants produce an iron-restricted growth defect phenotype, in for example human or animal sera. Using SbnA and SbnB mutants in growth culture assays, compounds were added to the growth media and tested for the ability to overcome the iron-restricted phenotype. FIG. 11 shows that proline is unable to overcome the iron-restricted growth defect of the SbnB mutant indicating that proline is not a product of an SbnB mediated enzymatic reaction that is used in staphylobactin biosynthesis. The iron-restricted growth defect of *S. aureus* SbnA and SbnB mutants (due to the lack of production of staphylobactin) can be overcome by addition of 2,3-diamonpropionate to the growth media (FIG. 12; data not shown for the SbnA mutant). This data shows that the modified amino acid 2,3-diaminopropionate is a component of staphylobactin.

Without wishing to be limited by theory, SbnB, a putative ornithine cyclodeaminase (OCD) is believed to liberate $NH_3$ as it converts and cyclizes ornithine to proline. SbnA, a predicted O-acetyl-L-serine sulfhydrylase may use the $NH_3$ in a reaction that converts O-acetyl serine to 2,3-diaminopropionate (DAPA) in an $NAD^+$-dependent manner.

SbnA and SbnB have been overexpressed and purified and an HPLC-based assay comprising these two proteins has been developed. This HPLC-based assay has been used to show that the product DAPA is produced when SbnA and SbnB are put together with O-acetyl-serine, ornithine, and NAD+ as reaction substrates. DAPA is not made when either enzyme is used in isolation of the other. These results confirm the SbnA and SbnB-dependent consumption of ornithine and O-acetyl-L-serine and the concomitant appearance of proline and 2,3-diaminopropionate. Furthermore, the ability to monitor production of DAPA in this HPLC-based assay indicates that this assay can be used for high-throughput screening for inhibitors that target SbnA or SbnB enzymes.

Example 10

FhuC is an ATPase for Both Sir and Hts Siderophore Transporters

An FhuC mutant, strain H1071, was assayed to determine whether its iron-restricted growth defect could be overcome in the presence of either one of the siderophores, staphyloferrin A and staphyloferrin B, or in the presence of both siderophores. More specifically, the ability of supernatant concentrates of cell cultures producing one or both of the siderophores to promote the iron-restricted growth of the FhuC *S. aureus* mutant was assessed using siderophore plate bioassays.

The FhuC mutant showed no growth in the plate bioassay when using either siderophore alone or using both together. This data indicates that FhuC is the ATPase that energizes transport of both *S. aureus* siderophores.

Example 11

Biosynthesis of Staphyloferrin B

Experimental Procedures
Bacterial Strains, Plasmids, and Standard Growth Condition.
Bacterial strains and plasmids used in this study are described in Table 5.

TABLE 5

Bacterial strains, plasmids and oligonucleotides used in this study.

| Bacterial strains, plasmids, and oligonucleotides | Description[a] | Source or reference |
|---|---|---|
| *E. coli* | | |
| DH5α | F− φ80dlacZΔM15 recA1 endA1 nupG gyrA96 glnV44 thi-1 hsdR17($r_K^-$ $m_K^+$) λ− supE44 relA1 deoR Δ(lacZYA-argF)U169 | Promega |
| ER2566 | F− λ− fhuA2 [lon] ompT lacZ::T7 gene 1 gal sulA11 Δ(mcrC-mrr)114::IS10 R(mcr-73::miniTn10-Tet$^S$)2 R(zgb-210::Tn10)1 (Tet$^S$) endA1 [dcm] | New England Biolabs |
| BL21(DE3) | F− ompT gal dcm lon hsdS$_B$ ($r_B^-$ $m_B^-$) λ(DE3 [lacI lacUV5-T7 gene 1 ind1 sam7 nin5]) | Novagen |

TABLE 5-continued

Bacterial strains, plasmids and oligonucleotides used in this study.

| Bacterial strains, plasmids, and oligonucleotides | Description[a] | Source or reference |
|---|---|---|
| *S. aureus* | | |
| RN4220 | $r_K^- m_K^+$; accepts foreign DNA | (Kreiswirth et al., 1983) |
| RN6390 | Prophage-cured wild type strain | (Peng et al., 1988) |
| H306 | RN6390 sirA; Km$^R$ | (Dale et al., 2004b) |
| H1324 | RN6390 Δsbn; Tet$^R$ | (Beasley et al., 2009) |
| H1661 | RN6390 Δsfa; Km$^R$ | (Beasley et al., 2009) |
| H1649 | RN6390 Δsbn Δsfa; Tet$^R$ Km$^R$ | (Beasley et al., 2009) |
| H1448 | RN6390 Δhts; Tet$^R$ | (Beasley et al., 2009) |
| H1480 | RN6390 sirA Δhts; Tet$^R$ Km$^R$ | (Beasley et al., 2009) |
| Plasmids | | |
| pET28a(+) | Overexpression vector for hexahistidine-tagged proteins; Km$^R$ | Novagen |
| pSbnC | pET28a(+) derivative encoding SbnC; Km$^R$ | This study |
| pSbnE | pET28a(+) derivative encoding SbnE; Km$^R$ | This study |
| pSbnF | pET28a(+) derivative encoding SbnF; Km$^R$ | This study |
| pSbnH | pET28a(+) derivative encoding SbnH; Km$^R$ | This study |

*E. coli* were grown in Luria-Bertani broth (Difco). For experiments not directly involved in the analysis of iron uptake, *S. aureus* was grown in tryptic soy broth (Difco). Tris-minimal succinate (TMS) was prepared as described (Sebulsky et al., 2004) and used as an iron-limited minimal medium. To further restrict the level of free iron in TMS, the iron chelating compounds 2,2'-dipyridyl and ethylene diamine-di(o-hydroxyphenol acetic acid) (EDDHA) were added as indicated in the text. Where necessary, kanamycin (30 μg/ml) was incorporated into media for the growth of *E. coli* strains. For *S. aureus*, kanamycin (50 μg/ml), neomycin (50 μg/ml) and tetracycline (4 μg/ml) were incorporated into growth media as required. Solid media were obtained by the addition of 1.5% (w/v) Bacto agar (Difco). All bacterial growth was conducted at 37° C. unless otherwise stated. Iron-free water for preparation of growth media and solutions was obtained by passage through a Milli-Q water filtration system (Millipore Corp.).

Recombinant DNA Methodology

Standard DNA manipulations were performed. Restriction endonucleases and DNA-modifying enzymes were purchased from Roche Diagnostics (Laval, Quebec, Canada), New England Biolabs (Mississauga, Ontario, Canada), Life Technologies Inc. (Burlington, Ontario, Canada) and MBI Fermentas (Flamborough, Ontario, Canada). Plasmid DNA was purified using QIAprep plasmid spin columns (QIAgen Inc., Santa Clarita, Calif.) as described by the manufacturer. Polymerase chain reactions were performed using PwoI DNA polymerase (Roche Diagnostics).

Siderophore Plate Bioassays

Siderophore plate bioassays were performed as described (Beasley et al., 2009). Growth promotion, as measured by the diameter of the growth halo around each disk, was determined after 36 h incubation at 37° C.

Bacterial Growth Curves

Bacteria were cultured for 12 hours in TMS broth then 12 hours in TMS broth containing 100 μM 2,2'-dipyridyl (Sigma-Aldrich). Cells were washed twice in saline, and diluted 1:100 into 60% horse serum (Sigma-Aldrich)—40% TMS broth. For iron-replete media, 50 μM FeCl$_3$ was included. Cultures were grown under constant, medium amplitude shaking in a Bioscreen C machine (Growth Curves, USA). Optical density was measured at 600 nm every 30 min. However, for clarity of growth curve figures, data are shown only at 2-hour intervals.

Siderophore Detection

To measure levels of siderophore activity, chrome azurol S (CAS) shuttle solution was prepared as described. In the case of in vitro synthesized staphyloferrin B, 50 μL of the reaction mixture were removed and diluted in 450 μL of deionized water followed by 500 μL of CAS shuttle solution in a 1 ml spectrophotometer cuvette. The mixture was then incubated in the dark for 45 minutes. Siderophore quantification and absorbance readings were performed as described (Beasley et al., 2009).

Protein Overexpression and Purification

Proteins were expressed in *E. coli* BL21 (DE3) by cloning the coding regions, amplified from the genome of *S. aureus* Newman using primers described in Table 1, into pET28a(+). *E. coli* cells containing expression constructs were grown to mid-log phase at 37° C. with aeration before IPTG (isopropyl-β-D-thiogalactopyranoside) (0.5 mM) was added, and cells cultured for an additional 16 h at room temperature. The cells were resuspended in 50 mM HEPES buffer (pH 7.4), 500 mM NaCl, 10 mM imidazole and lysed in a French pressure cell at 10,000 psi, and the lysate was centrifuged at 15,000×g for 15 min to remove unbroken cells and debris, prior to centrifugation at 150,000×g for 60 min to remove insoluble material. The soluble sample was applied to a 1 ml HisTrap nickel affinity (GE Healthcare) column equilibrated with buffer A, and the 6×His-tagged proteins were eluted from the column with a gradient of 0-80% buffer B over 20 column volumes; Buffer A contained 50 mM HEPES buffer (pH 7.4), 500 mM NaCl, 0 mM imidazole, buffer B contained 50 mM HEPES buffer (pH 7.4), 500 mM NaCl, 500 mM imidazole. Proteins were dialyzed into 50 mM HEPES (pH 7.4), 150 mM NaCl and 10% glycerol at 4° C. Protein purity was confirmed using ESI-MS and sodium dodecyl sulfate-polyacrylamide gel electrophoresis. Protein yield from the induced cultures harbouring the expression constructs was determined to be 1.5 mg/L (SbnC), 1.5 mg/L (SbnE), 3 mg/L (SbnF) and 17 mg/L (SbnH).

Mass Spectrometry

LC-MS and LC-MS/MS analyses of concentrated culture supernatant samples were performed as described previously (Beasley et al., 2009).

For analysis of in vitro reaction products, enzymes were first removed using centricon with molecular weight cutoff of 10000. Effluent was injected onto the LC-MS/MS system, consisting of a Waters CapLC with a Phenomenex Jupiter Proteo 90 A column (150×1.0 mm, 4 µm) coupled to a Q-TOF (micro, Waters) mass spectrometer. Separation was carried out at a flow rate of 40 µL/min with a gradient starting at 1% B and increase to 50% B in 15 min and then to 95% B in 5 min, and hold for 5 min. Solvent A was water and solvent B was 95% acetonitrile, both with 0.1% formic acid. LC-ESI-MS analysis was performed in negative ion mode with a scan range of 200 to 700 m/z. Collision induced dissociation was performed with a mass range of 60 to 500 m/z using argon as the collision gas. Variable collision energy of 20 to 30 volts was applied to obtain an informative fragmentation spectrum. Data were acquired and analyzed by MassLynx 4.0 (Micromass).

In Vitro Staphyloferrin B Biosynthesis

Reactions, in a total volume of 100 µL, consisted of 5 mM ATP, 0.5 mM MgCl$_2$, 1 mM Dap HCl, 1 mM sodium citrate, 1 mM ethylenediamine, 1 mM α-KG, 5 µM SbnC, 5 µM SbnE, 5 µM SbnF, and buffered in 50 mM HEPES pH 7.4. When assessing the ability of Dae to substitute the need for SbnH, 1 mM Dae was added to replace the SbnH and pyridoxal-5'-phosphate components of the above reaction mixture. Reactions were incubated overnight at room temperature in the dark.

Substrate Selectivity (Hydroxanate Formation) Assays

All reactions were performed in 300 µL volumes and the following were common to each reaction: 2.25 mM ATP, 15 mM MgCl$_2$, 150 mM hydroxylamine, and 50 mM HEPES pH 7.4. To assess which enzyme utilized citrate as a substrate, 5 µM of SbnC, SbnE, or SbnF were incubated with 3 mM citrate and the common reaction components as described above. Similarly, to assess which enzyme utilized α-KG as a substrate, 5 µM of SbnC, SbnE, or SbnF were incubated with 3 mM α-KG and the common reaction components. To assess the potential recognition of citryl-Dae as a substrate by SbnF or SbnC, this intermediate was formed in overnight reactions containing 2.25 mM ATP, 15 mM MgCl$_2$, 3 mM sodium citrate, 50 mM Dae, 5 µM SbnE buffered in 50 mM HEPES pH 7.4. This reaction was then heat treated at 70° C. to deactivate SbnE and the reaction was then centrifuged at 14 500 rpm for 10 minutes to pellet precipitated enzyme. The supernatant which now contains the citryl-Dae intermediate was incubated with fresh 5 µM SbnF or SbnC, 2.25 mM ATP, and 150 mM hydroxylamine. To assess the potential recognition of citryl-Dap as a substrate for SbnF or SbnC, this intermediate was formed as described above except that Dae was replaced with 50 mM Dap instead. For each reaction, a duplicate control reaction was prepared in which the enzyme was previously inactivated by heating at 100° C. for 10 minutes. All reactions described above were incubated at room temperature in the dark for 1 hour before addition of 300 µL stopping solution which consisted of 10% (w/v) FeCl$_3$ and 3.3% (w/v) trichloroacetic acid in 0.7 M HCl. Reactions were centrifuged at 20 000×g for 5 minutes to remove precipitate and the formation of ferric hydroxamate was detected spectrophotometrically at 540 nm. Relative absorbance values reported in this study were calculated by subtracting the absorbance of the control (boiled enzyme) reactions from the absorbance of experimental reactions.

Determination of Kinetics for SbnE (i) Determination of Extinction Coefficient for Citryl-Hydroxamate A series of reactions, incubated overnight and containing 2.25 mM ATP, 15 mM MgCl$_2$, 150 mM hydroxylamine, 50 mM HEPES pH 7.4, and 5 µM SbnE, were tested against a range of sodium citrate concentrations ranging from 100 µM to 30 mM. After addition of stopping solution and measurement of absorbance at 540 nm, a linear relationship between absorbance and concentration of sodium citrate was established. The extinction coefficient of the citryl-hydroxamate was determined to be 0.45 mM$^{-1}$cm$^{-1}$.

(ii) Determination of K$_m$, Vmax and k$_{cat}$

To determine the kinetic parameters of SbnE catalysis, 500 µM citrate was incubated with 2.25 mM ATP, 15 mM MgCl$_2$, 150 mM hydroxylamine, 50 mM HEPES pH 7.4, and 3 µM SbnE. The resulting product conversion rate was still linear at 10 minutes and gave an approximately 14% substrate-to-product conversion. Therefore, reaction rates were measured spectrophotometrically at the 10-minute timepoint with citrate concentrations ranging from 0.25 mM to 30 mM. Reaction rate values at each citrate concentration were fitted to the Michaelis-Menten equation and analyzed by non-linear regression. Due to the limit of detection and instability of the hydroxamate product formed by SbnC, the kinetic parameters for this enzyme were not evaluated.

Computer Analyses

DNA sequence analysis and PCR oligonucleotide primer design were performed using Vector NTI Suite (Informax, Inc.) and MacVector software packages. Graphpad Prism was used for data analysis and graphing applications.

Results

The S. aureus sbn Operon is Associated with Production of Staphyloferrin B.

The products of the sbn operon in S. aureus were used to synthesize staphyloferrin B. Iron-starved spent culture supernatant from S. aureus H1661 (RN6390 Δsfa) (note: a staphyloferrin A-deficient genetic background was used to simplify siderophore extraction and analysis) was analyzed for the presence of staphyloferrin B, and compared to that of S. aureus H1649 (RN6390 ΔsfaΔsbn). Staphyloferrin B ([M-H]$^-$=447.14) was detected in the iron-starved spent culture supernatant of H1661, but not H1649, confirming that the sbn operon is involved in the synthesis of this siderophore. Previous results demonstrated that culture supernatants of H1661, but not H1649, could promote the iron-starved growth of S. aureus, as would be expected should H1661 synthesize a molecule with siderophore properties.

In Vitro Synthesis of Staphyloferrin B

Bioinformatic analyses of the predicted protein products from the staphyloferrin B biosynthesis operon identified three enzymes (SbnC, SbnE and SbnF) that belong to the NIS family of siderophore synthetase enzymes. These enzymes are thought to catalyze the ATP and Mg$^{2+}$-dependent activation of carboxylate substrates, in a reaction that proceeds through an acyl-adenlyate intermediate that is then recognized by an amine substrate to yield an overall condensation reaction to an amide. To examine the activity of the SbnC, SbnE and SbnF enzymes, and to determine their role in staphyloferrin B synthesis, each was independently overexpressed in E. coli as a hexahistidine-tagged derivative, and subsequently purified using nickel-affinity chromatography.

When the three synthetases were incubated together with staphyloferrin B components L-2,3-diaminopropionic acid (Dap), citrate, 1,2-diaminoethane (Dae), and α-ketoglutarate (α-KG), an ion corresponding to staphyloferrin B was not formed. Additional purified Sbn enzymes were added to the reaction. Notably, when SbnH, a putative PLP-dependent decarboxylase, was combined in reactions with the three synthetases and substrates, an ion corresponding to that of staphyloferrin B was produced. The staphyloferrin B ion was not produced when any of ATP, $Mg^{2+}$, SbnC, SbnE, SbnF, SbnH, Dap, citrate or α-KG was omitted from the reaction (data not shown). Notably, staphyloferrin B synthesis could proceed without the addition of Dae in the reaction. ESI-MS/MS was used to confirm that staphyloferrin B produced in vitro was the same as that isolated from spent culture supernatants of iron-starved S. aureus.

In Vitro-Synthesized Staphyloferrin B is Biologically Active

Figure 13:
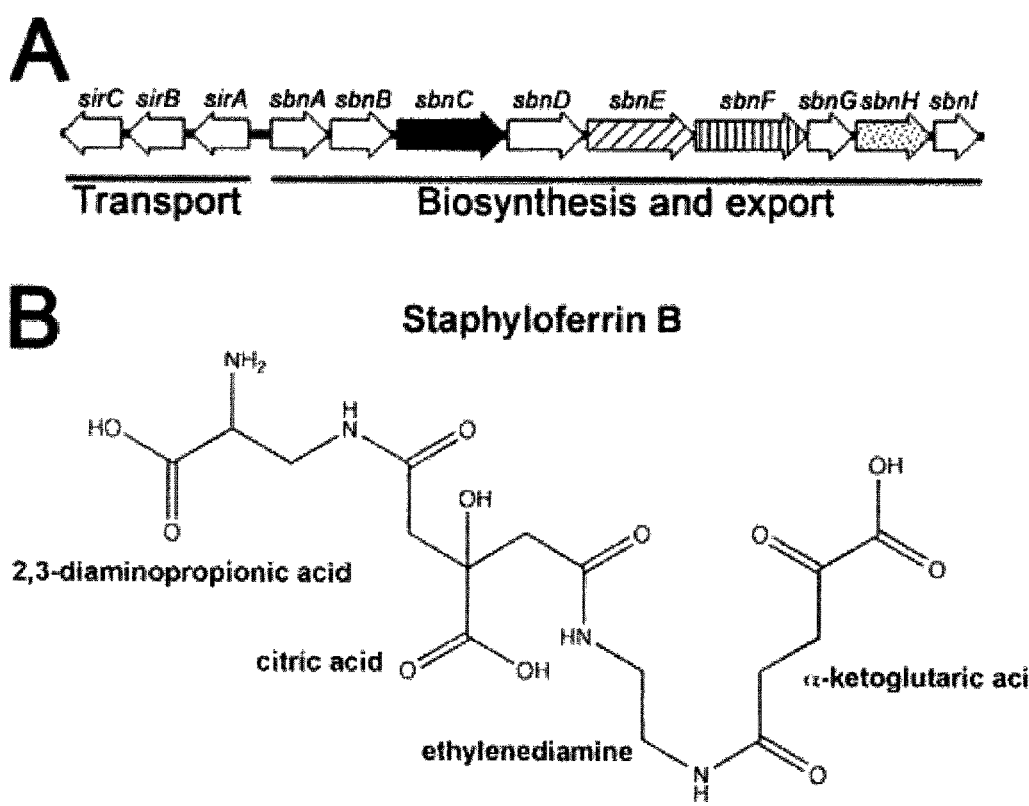
FIG. 13 illustrates a physical map of the *S. aureus* sir-sbn genetic locus identifying type A (angle lines), type B (solid) and type C (vertical lines) NIS synthetases and a decarboxylase (dotted), and the structure of staphyloferrin B (B)
Figure 14:
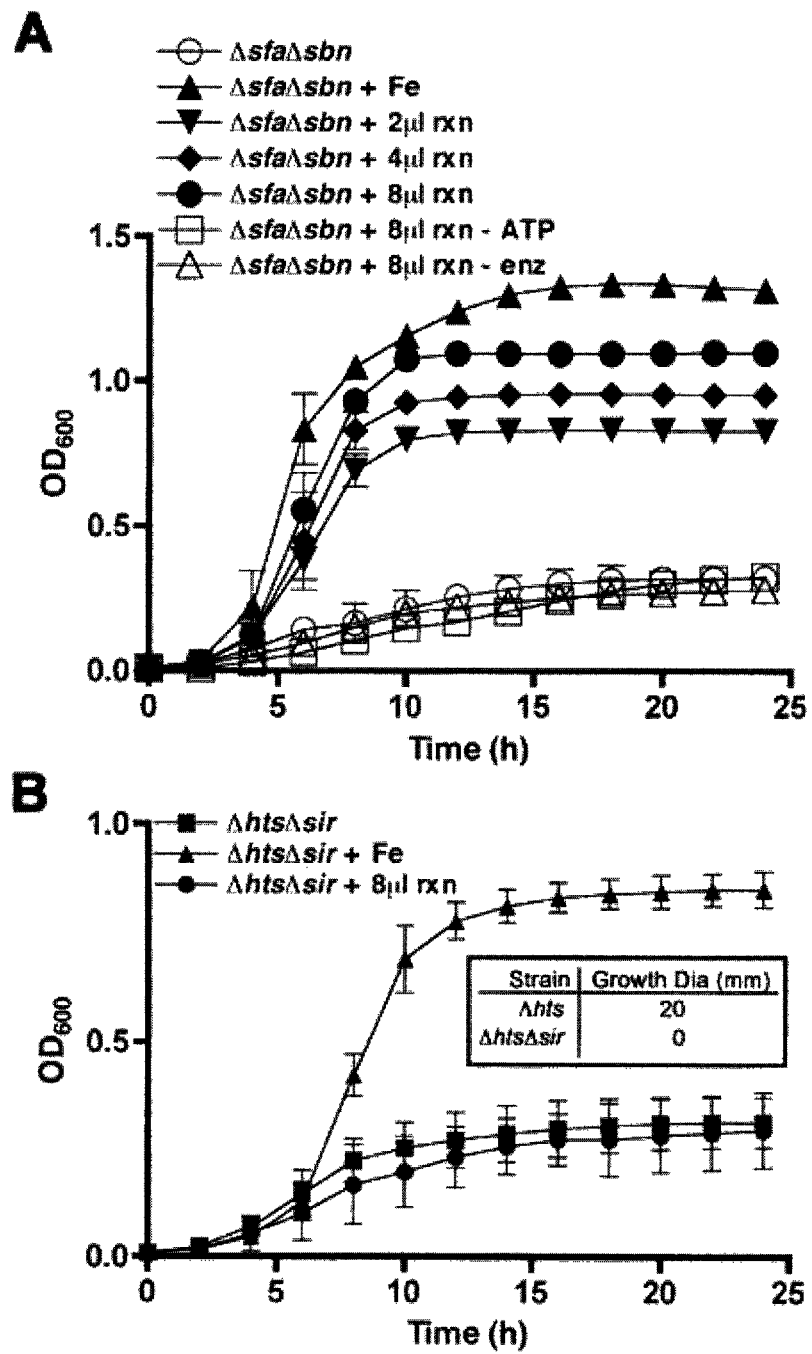
FIG. 14 graphically illustrates bacterial growth of iron-starved *S. aureus* Δsbn/Δsbt mutant in the presence of increasing amounts of staphyloferrin B (SB) synthesized in vitro reaching levels comparable to growth in the presence of iron (A); and graphically compares bacterial growth of a ΔsfaΔsbn mutant in the presence and absence of iron, and in the presence of staphyloferrin B with no iron (B)

Having established that staphyloferrin B can be produced in vitro, it was important to show that the molecule had the same biological properties (i.e. the ability to deliver iron to bacteria) as that of staphyloferrin B produced by S. aureus cells. This was confirmed by showing that enzymatic reaction material derived from complete reactions (i.e. those containing citric acid, Dap, α-KG, ATP, $Mg^{2+}$, and SbnCEFH), and not incomplete reactions (i.e. lacking ATP or enzymes), could readily promote the iron-starved growth of siderophore-deficient S. aureus (i.e. ΔsfaΔsbn) in a concentration-dependent fashion (FIG. 14A). This staphyloferrin B-dependent growth promotion was mediated by the ABC transporter SirABC (FIG. 14B), which is encoded by the sirABC operon divergently transcribed from the sbn operon (FIG. 13A).

SbnE, a Citrate Desymmetrizing Enzyme, Initiates Staphyloferrin B Synthesis

S. aureus SbnE is 578 amino acids in length with a calculated molecular mass of 66 kDa and an estimated pI of 5.52. Gel filtration analyses demonstrates that the protein exists in solution as a dimmer. Bioinformatic analyses place the enzyme in the lucA/lucC family of NRPS-independent siderophore (NIS) synthetases and, more specifically, into the type A subfamily. The type A enzymes are specific for condensation reactions involving citric acid, catalyzing the stereospecific adenylation of one of the prochiral carboxymethyl groups of citrate, priming it for reaction with L-serine to form an achromobactin precursor.

Figure 15:
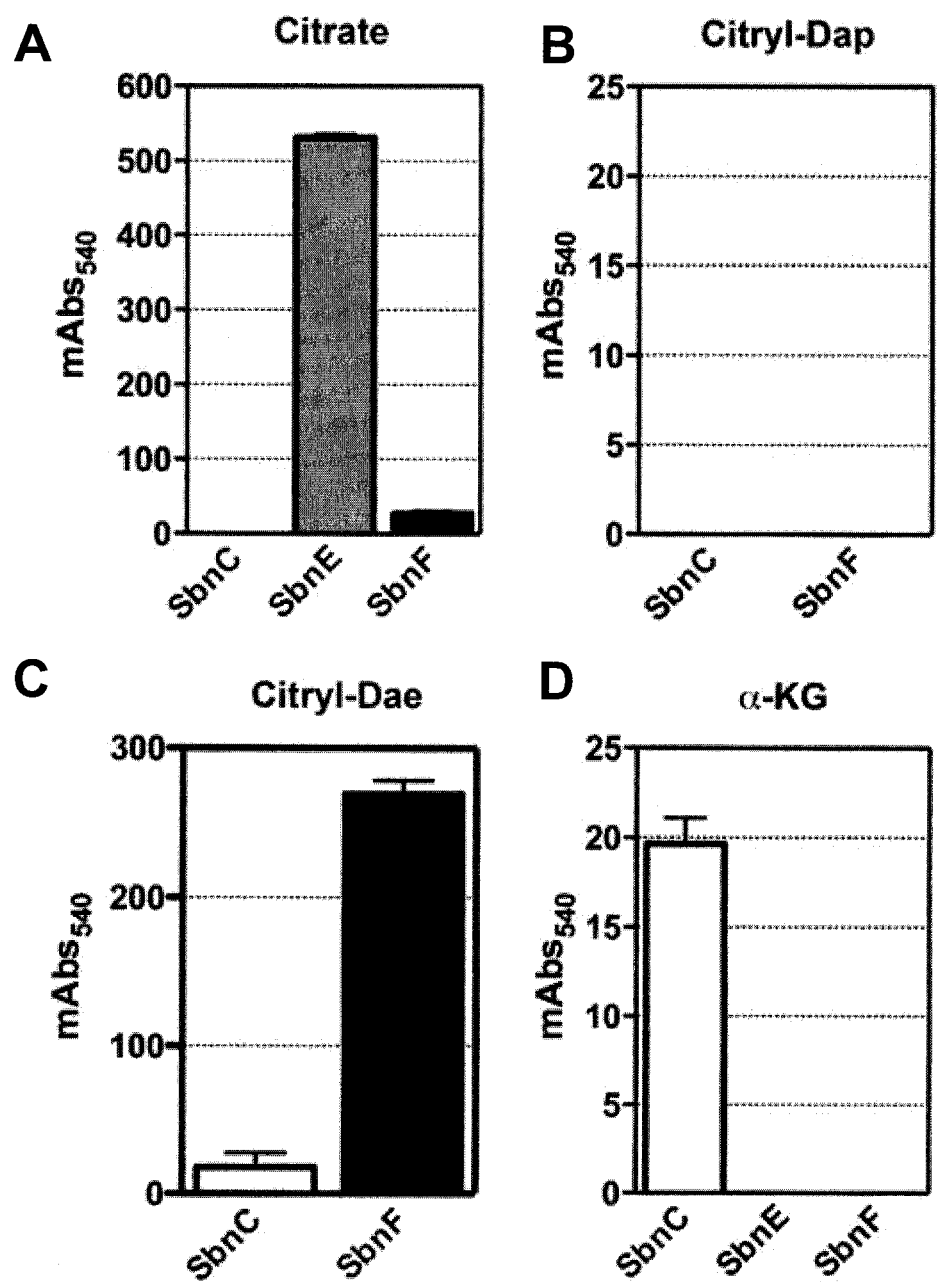
FIG. 15 provides bar graphs illustrating substrate specificity of Sbn enzymes for the carboxylic acid substrates, citrate (A), citryl-Dap (B), citryl-Dae (C) and α-KG (D)

To assay for enzymatic activity of SbnE, the hydroxylamine trapping assay (described in Kadi & Challis, 2009) was used. Essentially, this assay is used to monitor the specific activity of a synthetase towards a particular carboxylic acid. As illustrated in FIG. 15, of the three NIS synthetases tested (SbnC, SbnE, and SbnF), only SbnE showed a high level of specific activity towards citrate as a substrate. In the structure of staphyloferrin B (FIG. 13B), citrate is joined on either side by Dap and Dae. Condensation of citrate with Dap or Dae would yield ion species of $[M-H]^-=277.08$ or $[M-H]^-=233.09$, respectively. LC-MS was used to demonstrate that SbnE incubated with citrate and Dae did not yield a species with m/z of 233.09 in negative ion mode. On the contrary, upon incubation with citrate and Dap, SbnE catalyzed the ATP-dependent formation of [3] ($[M-H]^-=277.08$). This species would result from the SbnE-catalyzed condensation of citrate and Dap to form a β-citryl-Dap intermediate. This reaction product reacted strongly with CAS reagent but was unable to promote the iron-starved growth of S. aureus (data not shown). The SbnE-dependent condensation of citrate with Dap was further confirmed by the appearance of an ion increased in size by 2 amu when citric acid-1,5-$^{13}C_2$ replaced citric acid in the reaction. SbnF, which showed a small level of activity towards citrate in hydroxylamine assays (FIG. 15), was unable to form the β-citryl-Dap intermediate.

The kinetics of the recognition of citrate by SbnE were determined using the hydroxylamine trapping assay, and were as follows: $K_m=0.99$ mM±0.12, $V_{max}=0.04$ mM/min±0.002, and $K_{cat}=16.08$ l/min±0.87. Michaelis-Menten kinetics were observed out to substrate concentrations as high as 30 mM citrate.

It was of interest to determine if SbnE could also carry out a condensation reaction between citrate and Dae. It was determined that this reaction does occur, but that when presented with equimolar concentrations of citrate, Dap and Dae, SbnE readily forms the citryl-Dap intermediate ($[M-H]^-=277.1$) and virtually no mass ion species that would correlate with the formation of citryl-Dae ($[M-H]^-=233.1$). Therefore, this suggests that Dap is the preferred amine substrate for SbnE.

SbnH Carries Out Pyridoxal-5'-Phosphate (PLP)-Dependent Decarboxylation of the Citryl-Dap Intermediate SbnH is 400 amino acids in length and has a mass of 45.8 kDa and an estimated pI of 5.85. As described above, the data demonstrated the sine qua non role of SbnH in staphyloferrin B (SB) synthesis. It was of interest, therefore, to define at which step decarboxylation occurs in the pathway. As mentioned above, in the presence of SbnCEFH, SB biosynthesis was dependent on the presence of substrates citric acid, Dap and α-KG, but not Dae. This is noteworthy because decarboxylation of Dap produces Dae. SbnH-dependent decarboxylation of free Dap by SbnH is unlikely to occur, however, based on the fact that SbnCEF-containing enzyme reactions containing Dae, but lacking SbnH, do not result in the formation of SB, indicating that free Dae is not incorporated into the structure. When SbnH was added to reactions containing SbnE, citric acid, and Dap, a species with $[M-H]^-$ of 233.09 appeared, in agreement with a decarboxylation reaction on [3] to yield [4] (see FIG. 16). Further evidence of this SbnH-dependent intermediate is the appearance of a species at $[M-H]^-=235.09$ in reactions where citric acid-2,4-$^{13}C$, replaced citric acid.

SbnF is Necessary to Form a Staphyloferrin B Intermediate

Figure 16:
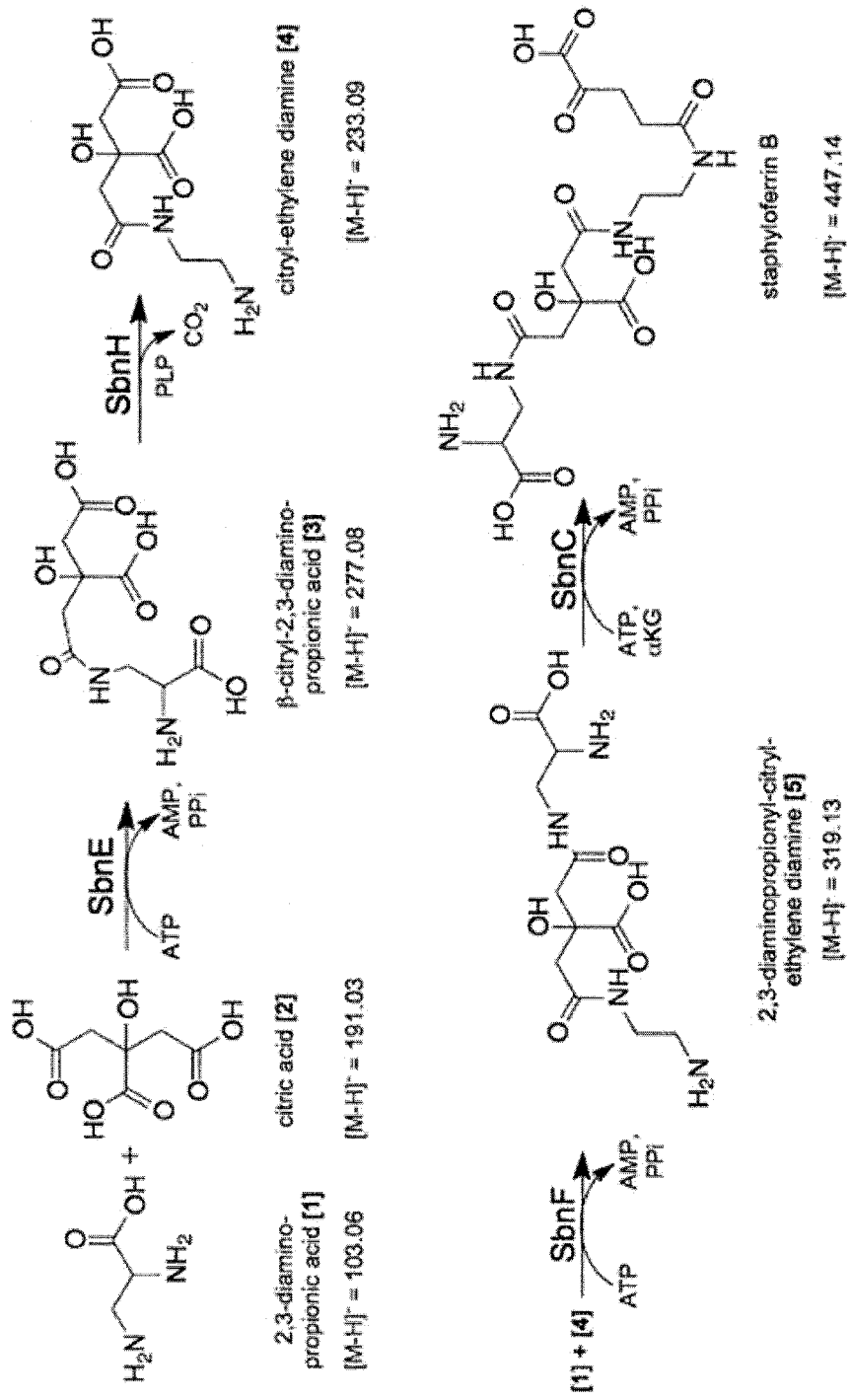
FIG. 16 illustrates a proposed scheme for the biosynthesis of staphyloferrin B.

SbnF is a 592-amino acid long protein with a theoretical mass of 68.9 kDa and an estimated pI of 5.07. Gel filtration analyses indicate that SbnF is a dimmer in solution. Bioinformatic analyses, along with the known structure of staphyloferrin B, indicate that SbnF, a putative type C synthetase, generates an amide bond between an amino or hydroxyl-containing substrate and a second substrate which is already a monoamide but which still possesses a free prochiral carboxyl. Thus, given that the data obtained were consistent with the generation of [4] from a reaction containing SbnE, SbnH, citrate and Dap, it was postulated that SbnF could act on this intermediate to add a molecule of Dap, which would be consistent with the known structure of Staphyloferrin B (SB). The potential substrate was first examined using substrate trapping (hydroxylamine) assays. Not surprisingly, SbnF did not react with the citryl-Dap product of a reaction containing SbnE, citrate and Dap (the mass ion 277.1 corresponding to [3]). It was next attempted to use the product of reactions containing SbnE, SbnH, citrate and Dap (which yields a mass ion of 233.1 consistent with citryl-Dae [4]). Unfortunately, it was determined that PLP, which is associated with SbnH, interfered with the assay. To overcome this, citryl-Dae was generated by reacting SbnE with citrate in the presence of a 17-fold molar excess Dae compared to routine reactions set up for LC-MS experiments. In this case, SbnF showed high levels of activity with the citryl-Dae intermediate. In the structure of SB, the Dae molecule is linked to citrate and Dap. Therefore, it was reasonable to assume that SbnF recognized and condensed the citryl-Dae intermediate with Dap. This reaction would generate a species of $[M-H]^-=319.1$. LC-MS confirmed that this species appeared in ATP-dependent reactions containing SbnE, SbnH, SbnF, citrate and Dap. Mass ions of 233.1 and 277.1 were also detectable in these reactions. When complete reactions contained citrate-2,4-$^{13}C_2$ in place of citrate, the 233.1, 277.1 and 319.1 mass ions were each shifted 2 mass units higher. Consistent with the hydroxylamine assay results showing that SbnF did not react with the SbnE-catalyzed citryl-Dap product, a mass ion of 363.1 (Dap-citryl-Dap) was not detected when SbnF was reacted with SbnE, citrate and Dap (data not shown). All together, the data are consistent with SbnF acting in the pathway subsequent to SbnE and SbnH, and generating [5] by condensing one molecule of Dap with [4] (FIG. 16).

SbnC Activates α-KG in a Reaction that Completes the Synthesis of Staphyloferrin B SbnC is 584 amino acids long with a mass of 66.4 kDa and an estimated pI of 4.93. Using gel filtration chromatography, SbnC was determined to be a dimer in solution. SbnC groups with type B synthetases based on bioinformatic analyses, meaning that it putatively catalyzes amide bond formation between an amino or hydroxyl group of one substrate and the C5 carboxyl group of α-KG. The hydroxylamine-trapping assay showed that SbnC, but not SbnE or SbnF, activates α-KG (FIG. 15). LC-MS was then used to demonstrate that enzyme reactions containing α-KG, citrate, Dap, SbnE, SbnH and SbnF (i.e. lacking SbnC) do not form staphyloferrin B (no species with m/z=447.1 in negative ion mode detectable above background) but do form an ion species that correlates with compound [5] (FIG. 16). These results suggest that SbnC condenses α-KG with 151 in the final step of staphyloferrin B biosynthesis (FIG. 16).

Discussion

Staphyloferrin A is comprised of two molecules of citric acid that are each amide linked to a single D-ornithine molecule. The gene cluster encodes two NIS synthetases (SbtB and SbtD), an amino acid racemase (SbtC) (presumably specific for L-ornithine) and a putative membrane embedded siderophore efflux protein (SbtA). In the biosynthesis of staphyloferrin A, SbtD appears to initiate synthesis using ATP-dependent adenylation of citric acid to form an intermediate which is captured by the 6-amine of D-ornithine in a condensation reaction that results in an amide-bond containing intermediate. In a similar reaction mechanism, SbtB appears then to catalyze the ATP-dependent condensation of a second citric acid molecule with the free amine of the δ-citryl-D-ornithine intermediate to form the final staphyloferrin A siderophore structure.

The biosynthesis of staphyloferrin B, composed of L-2,3-diaminopropionic acid (Dap), citric acid, 1,2-diaminoethane (Dae), and α-KG, is synthesized in an NIS-dependent manner. The sbn gene cluster encodes three NIS synthetases (SbnCEF). As described herein, *S. aureus* sbt deletion mutants (i.e. do not synthesize staphyloferrin A) make readily detectable amounts of staphyloferrin B. Staphyloferrin B synthesis in *S. aureus* was dependent on the sbn genes since the siderophore was not detected in culture supernatants of a mutant containing deletions of both the sbt and sbn gene clusters.

In order to elucidate the staphyloferrin B biosynthetic pathway, Sbn proteins were purified and reacted with staphyloferrin B components. It is noteworthy that inclusion of the three synthetases (SbnCEF) along with ATP, $Mg^{2+}$ and the 4 component substrates of staphyloferrin B, in a one-pot assay, did not result in the formation of staphyloferrin B. Staphyloferrin B was only formed with the inclusion in the assay of the PLP-dependent decarboxylase, SbnH.

Example 12

Biosynthesis of Staphyloferrin A

Reaction products, SfaD, SfaB, D-ornithine, citrate, ATP and Mg2+, were placed on a paper disk which was placed on an agar plate impregnated with *S. aureus* that does not grow unless provided an iron source. Growth radius was measured around the disc after incubation of plates at 37° C. for 24 hours.

Figure 18:
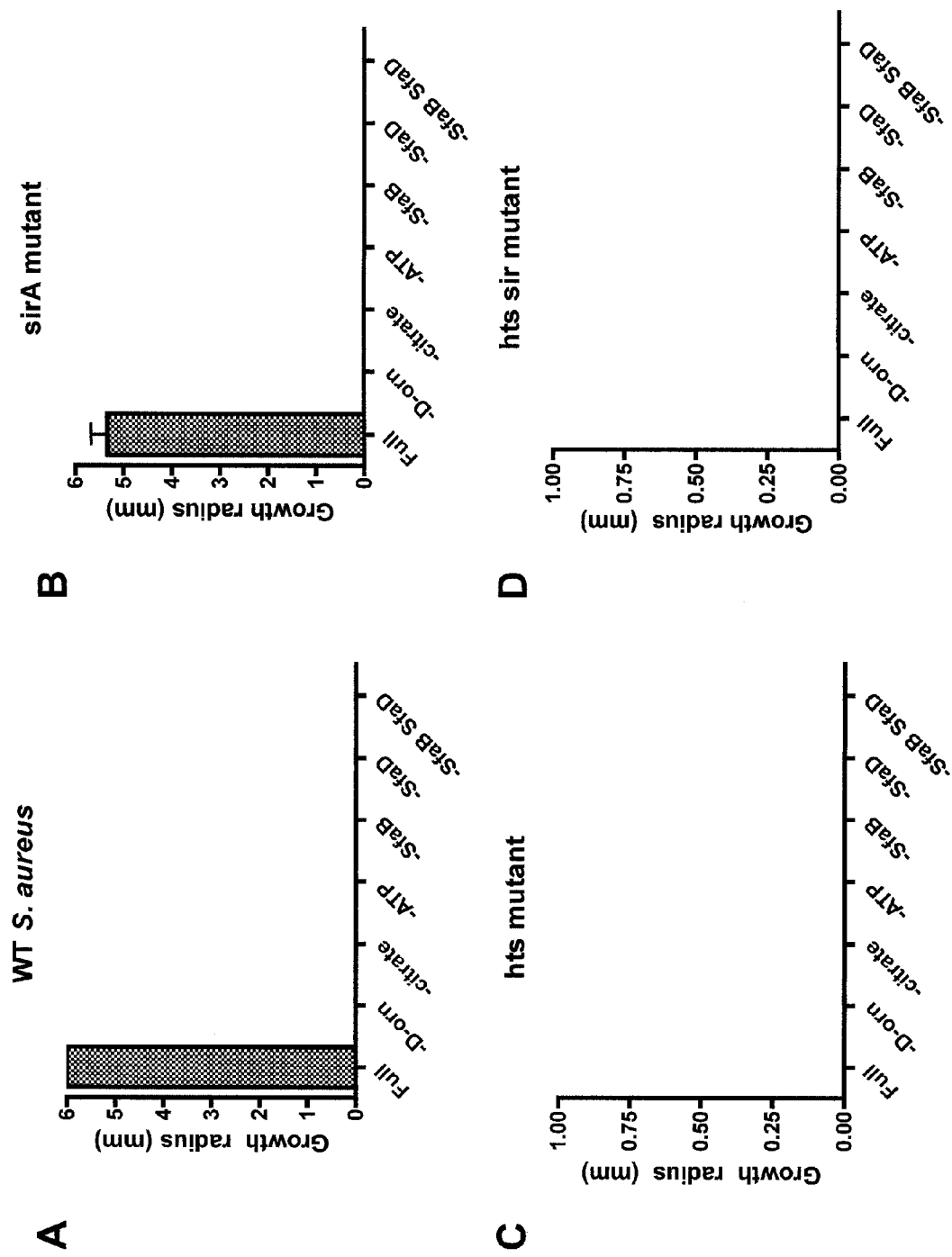
FIG. 18 provides bar graphs illustrating growth of wildtype *S. aureus* (A) and a SirA mutant (B), and, and no growth of Hts (C) and HtsSir mutants (D) in the presence of staphyloferrin A synthesized in vitro.

Staphyloferrin A synthesized in a cell-free system was found to be biologically active. It promoted growth of all strains that expressed the Hts transporter (specific for staphyloferrin A), namely, wildtype *S. aureus* (FIG. 18A) and SirA mutant (FIG. 18B), but did not promote growth of strains mutated for Hts, namely, an Hts mutant (FIG. 18C) and an HtsSir mutant (FIG. 18D).

Figure 19:
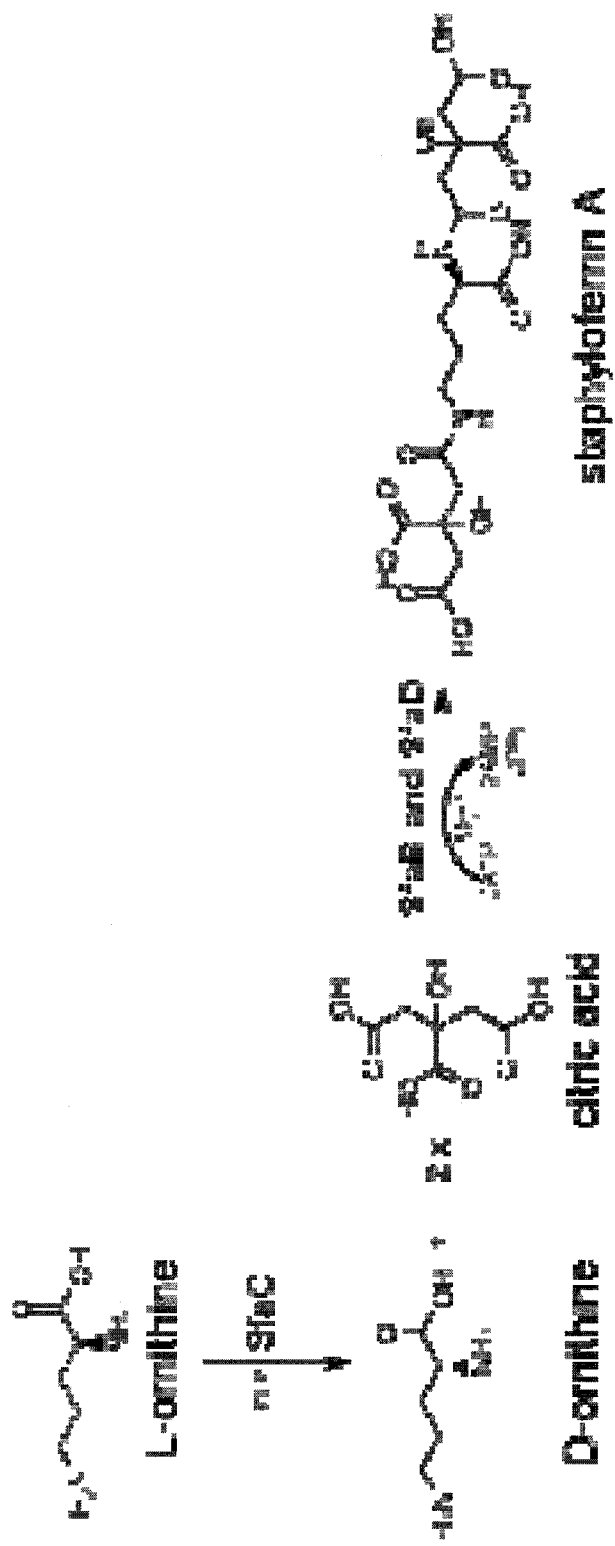
FIG. 19 illustrates a proposed scheme for the biosynthesis of staphyloferrin A.

The pathway of Staphyloferrin A biosynthesis is set out in FIG. 19.

Omitting any of one of SfaD, SfaB, D-ornithine, citrate, ATP and Mg2+ was found to obviate staphyloferrin A production.

Example 13

Hts and Sir Siderophore Binding Pockets

HtsA for crystallization was expressed from *E. coli* ER2566 cells grown at 30° C. to an optical density of □0.8 followed by induction with 0.5 mM IPTG and overnight incubation at 25° C. Cells were disrupted using an Emulsi-Flex-05 homogenizer (Avestin) and the soluble fraction was isolated after centrifugation at 100 000 g for 30 min. Soluble 6×His-HtsA was purified using a HisTrap column (GE Healthcare) and then the 6×His-tag was removed by thrombin digestion. Protein was further purified by cation exchange chromatography using a Source 15S column (GE Healthcare) equilibrated with 50 mM HEPES (pH 7.8) and a NaCl gradient (0-500 mM) for elution. HtsA was dialysed into 20 mM Tris (pH 8) for all crystallization experiments. Selenomethionine-labelled HtsA was produced by methods previously described (Van Duyne et al., 1993) and purified similarly native HtsA.

Apo-HtsA crystals were grown by hanging drop vapour diffusion at room temperature. Well solutions contained 0.1 M HEPES (pH 6.8) and 24-30% Jeffamine ED-2001. Hanging drops were made from 1 µl of a 25 mg ml-1 protein solution and 1 µl of well solution. Crystals were flash frozen in liquid nitrogen after brief immersion in well solution supplemented with 15% glycerol.

Single-wavelength anomalous diffraction data for selenomethionine-labelled protein crystals was collected at the Stanford Synchrotron Radiation Laboratory on beam line 7-1. The data were processed and scaled using Mosflm and SCALA. Crystals grew in the space group P21 with one molecule in the asymmetric unit. Phases were determined using Solve and Resolve with an initial figure of merit of 0.40 that was improved to 0.80 with density modification. An initial model was built using ArpWARP. Native protein crystal X-ray diffraction data were collected at the Canadian Light Source on beam line 08ID-1 and was processed and scaled using HKL2000. For both structures, manual building and refinement was completed using Coot and Refmac5, respectively. Crystallographic data and refinement statistics are shown in Table 6.

TABLE 6

Data collection and refinement statistics for the HtsA structure

|  | Native HtsA | Se-Met HtsA |
|---|---|---|
| Data collection[a] | | |
| Resolution range (Å) | 50-1.60 (1.66-1.60) | 50-1.35 (1.40-1.35) |
| Space group | $P2_1$ | $P2_1$ |
| Unit cell dimensions (Å) | a = 44.70, b = 43.57, c = 75.71, β = 100.6° | a = 44.95, b = 43.65, c = 76.04, β = 100.6° |
| Unique reflections | 38 161 | 63 781 |
| Completeness (%) | 96.8 (76.5) | 97.9 (87.3) |
| Average I/σI | 20.8 (6.0) | 37.9 (5.9) |
| Redundancy | 3.4 (2.6) | 3.4 (2.5) |
| $R_{merge}$ | 0.059 (0.166) | 0.050 (0.166) |
| Refinement | | |
| R-work (R-free) | 16.6 (20.1) | 13.0 (16.5) |
| No. of water molecules | 382 | 494 |
| Average B-value (Å$^2$) | 13.9 | 9.6 |
| r.m.s.d. bond length (Å) | 0.13 | 0.13 |
| Ramachandran plot, % residues | | |
| In most-favourable region | 92.5 | 91.4 |
| In disallowed regions | 0.0 | 0.0 |

[a]Values in parenthesis represent the highest resolution shell.

Figure 20:
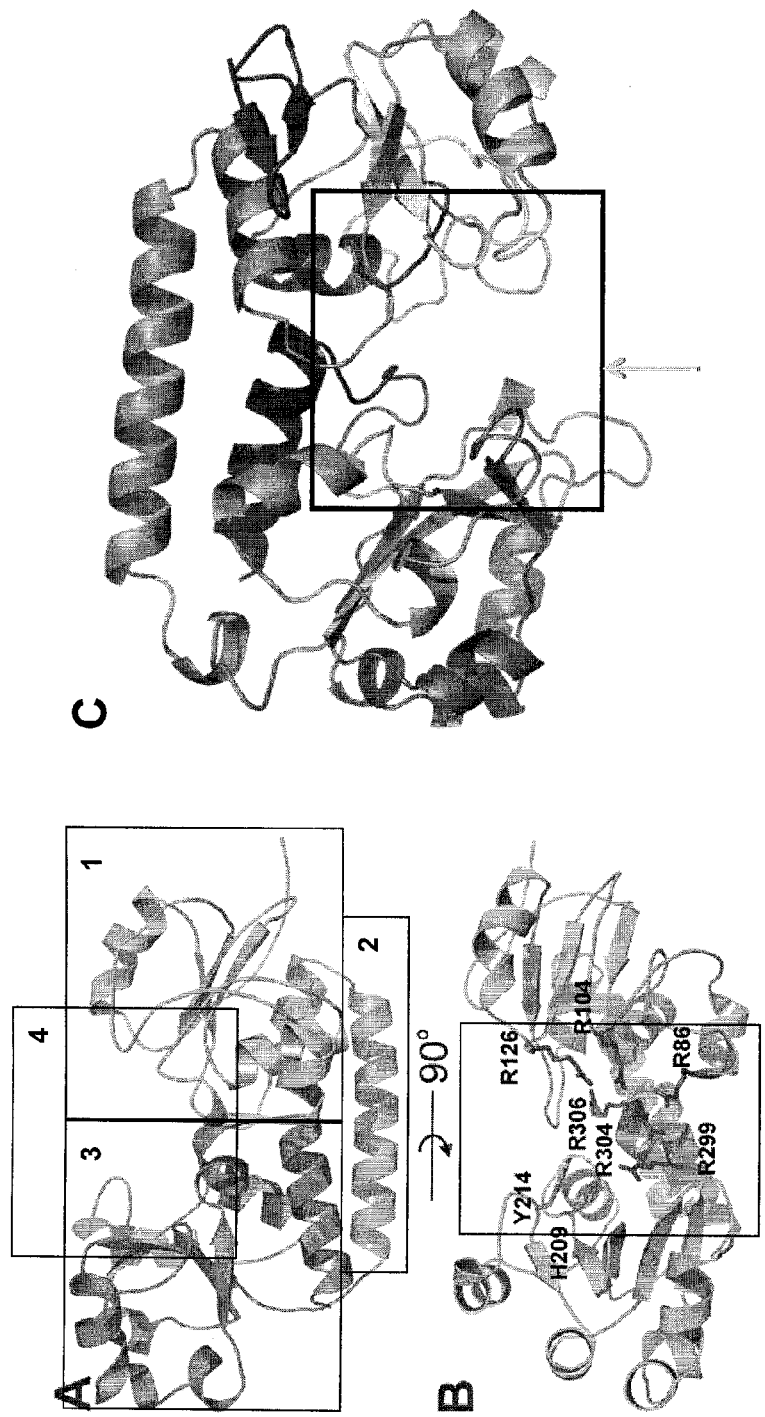
FIG. 20 provides schematics of the HtsA crystal structure identifying the staphyloferrin A binding region (box 4) (A) including residues within the binding region (B), and a schematic of the SirA crystal structure identifying the stapyloferrin B binding region (box) (C).

The structure consists of residues Thr-38-Lys-327, which excludes 15 N-terminal residues following the Cys-22 lipidation site that together likely form a flexible anchor. HtsA and SirA are comprised of mixed α/β N-terminal and C-terminal lobes bridged by a single α-helical backbone (FIG. 20). The ligand-binding groove is shallow and dominated by a large basic patch as shown in FIG. 20B. The overall fold places HtsA among the class III periplasmic binding protein family.

To investigate ligand binding within the groove, the ligand-bound CeuE, FhuD, ShuT, PhuT and IsdE structures were superposed onto HtsA, and SirA. When superposed, the ligands bound to these structures overlay in highly similar lateral locations within the binding groove. The corresponding region of HtsA contains a large patch of positive electrostatic potential contributed mainly by six Arg residues (Arg-86, 104, 126, 299, 304 and 306) that are directed into the groove (FIG. 20B). This arrangement of positively charged side-chains in the ligand-binding groove would favour an interaction with the anionic staphyloferrin A molecule. Staphyloferrin A coordinating residues are indicated to be Y214 and H209.

Together, this data indicates, for the first time, a region within HtsA and SirA that would serve as a target region for inhibiting the interaction of each of the Hts and Sir transport systems with siderophore for subsequent uptake has been identified.

REFERENCES

Bateman, B. T., Donegan, N. P., Jarry, T. M., Palma, M., and Cheung, A. L. (2001) Evaluation of a tetracycline-inducible promoter in *Staphylococcus aureus* in vitro and in vivo and its application in demonstrating the role of sigB in microcolony formation. *Infect Immun* 69: 7851-7857.

Chakraborty, T., Leimeister-Wachter, M., Domann, E., Hartl, M., Goebel, W., Nichterlein, T., and Notermans, S. (1992) Coordinate regulation of virulence genes in *Listeria monocytogenes* requires the product of the prfA gene. *J. Bacteriol.* 174: 568-574.

Dale, S. E., Doherty-Kirby, A., Lajoie, G., and Heinrichs, D. E. (2004a) Role of siderophore biosynthesis in virulence of *Staphylococcus aureus*: identification and characterization of genes involved in production of a siderophore. *Infect Immun* 72: 29-37.

Dale, S. E., Sebulsky, M. T., and Heinrichs, D. E. (2004b) Involvement of SirABC in iron-siderophore import in *Staphylococcus aureus*. *J Bacteriol* 186: 8356-8362.

Dobinsky, S., Bartscht, K., and Mack, D. (2002) Influence of Tn917 insertion on transcription of the icaADBC operon in six biofilm-negative transposon mutants of *Staphylococcus epidermidis*. *Plasmid* 47: 10-17.

Duthie, E. S., and Lorenz, L. L. (1952) Staphylococcal coagulase: mode of action and antigenicity. *J Gen Microbiol* 6: 95-107.

Guérout-Fleury, A. M., Shazand, K., Frandsen, N., and Stragier, P. (1995) Antibiotic-resistance cassettes for *Bacillus subtilis*. *Gene* 167: 335-336.

Kreiswirth, B. N., Lofdahl, S., Bentley, M. J., O'Reilly, M., Schlievert, P. M., Bergdoll, M. S., and Novick, R. P. (1983) The toxic shock syndrome exotoxin structural gene is not detectably transmitted by a prophage. *Nature* 305: 709-712.

Lee, C. Y., and Iandolo, J. J. (1986) Lysogenic conversion of staphylococcal lipase is caused by insertion of the bacteriophage L54a genome into the lipase structural gene. *J Bacteriol* 166: 385-391.

Lee, C. Y. (1992) Cloning of genes affecting capsule expression in *Staphylococcus aureus* strain M. *Molecular Microbiology* 6: 1515-1522.

Lee, J. W., and Heimann, J. D. (2007) Functional specialization within the Fur family of metalloregulators. *Biometals* 20: 485-499.

Li, J. M., Umanoff, H., Proenca, R., Russell, C. S., and Cosloy, S. D. (1988) Cloning of the *Escherichia coli* K-12 hemB gene. *J Bacteriol* 170: 1021-1025.

Muryoi, N., Tiedermann, M. T., Pluym, M., Cheung, J., Heinrichs, D. E., and Stillman, M. J. (2008) Demonstration of the iron-regulated surface-determinant (Isd) heme transfer pathway in *Staphylococcus aureus*. Submitted.

Peng, H. L., Novick, R. P., Kreiswirth, B., Kornblum, J., and Schlievert, P. (1988) Cloning, characterization, and sequencing of an accessory gene regulator (agr) in *Staphylococcus aureus*. *J. Bacteriol.* 170: 4365-4372.

Schwyn, B., and Neilands, J. B. (1987) Universal chemical assay for the detection and determination of siderophores. *Analytical Biochemistry* 160: 47-56.

Sebulsky, M. T., Hohnstein, D., Hunter, M. D., and Heinrichs, D. E. (2000) Identification and characterization of a membrane permease involved in iron-hydroxamate transport in *Staphylococcus aureus*. *J. Bacteriol.* 182: 4394-4400.

Skaar, E. P., Humayun, M., Bae, T., DeBord, K. L., and Schneewind, O. (2004) Iron-source preference of *Staphylococcus aureus* infections. *Science* 305: 1626-1628.

Yanisch-Perron, C., Vieira, J., and Messing, J. (1985) Improved M13 phage cloning vectors and host strains: nucleotide sequences of the M13mp18 and pUC19 vectors. *Gene* 33: 103-119.

The relevant portions of all documents referred to herein are hereby incorporated by reference.

We claim:

1. A method of inhibiting *S. aureus* comprising the steps of inhibiting staphyloferrin A-mediated iron uptake in *S. aureus* by inhibiting the expression or activity of at least one of SbtA, SbtB, SbtC and SbtD or at least one of HtsA, HtsB and HtsC; and inhibiting staphyloferrin B-mediated iron uptake in *S. aureus* by inhibiting the expression or activity of at least one of SbnA, SbnB, SbnC, SbnD, SbnE, SbnF, SbnG, SbnH, and SbnI or at least one of SirA, SirB and SirC.

2. The method as defined in claim 1, wherein Staphyloferrin A-mediated iron uptake is inhibited by disrupting the ligand binding region of HtsA.

3. The method as defined in claim 1, wherein Staphyloferrin B-mediated iron uptake is inhibited by disrupting the ligand binding region of SirA.

4. The method as defined in claim 1, wherein the expression of at least one of SbtA, SbtB, SbtC, SbtD, SbnA, SbnB, SbnC, SbnD, SbnE, SbnF, SbnG, SbnH and SbnI is inhibited with an enzyme inhibitor.

5. The method as defined in claim 4, wherein the inhibitor is a racemase, decarboxylase or synthetase inhibitor.

6. The method as defined in claim 1, wherein *S. aureus* is inhibited by inhibiting the expression of at least one of SbtA, SbtB, SbtC and SbtD and at least one of SbnA, SbnB, SbnC, SbnD, SbnE, SbnF, SbnG, SbnH, and SbnI.

7. The method of claim 6, wherein the expression of each of SbtA, SbtB, SbtC and SbtD and each of SbnA, SbnB, SbnC, SbnD, SbnE, SbnF, SbnG, SbnH, and SbnI is inhibited.

8. The method as defined in claim 1, wherein *S. aureus* is inhibited by inhibiting the expression or activity of at least one of HtsA, HtsB and HtsC, and the expression of at least one of SirA, SirB and SirC.

9. The method as defined in claim 8, wherein *S. aureus* is inhibited by inhibiting the expression or activity of each of HtsA, HtsB and HtsC, and the expression of SirA.

10. The method of claim 1, wherein staphyloferrin A-mediated iron uptake and staphyloferrin B-mediated iron uptake is inhibited using antisense oligonucleotides.

11. A method of inhibiting *S. aureus* comprising inhibiting staphyloferrin A-mediated iron uptake and staphyloferrin B-mediated iron uptake in *S. aureus* by inhibiting expression of FhuC.

* * * * *

SEQUENCE LISTING

<160> NUMBER OF SEQ ID NOS: 29

<210> SEQ ID NO 1
<211> LENGTH: 33
<212> TYPE: DNA
<213> ORGANISM: Artificial
<220> FEATURE:
<223> OTHER INFORMATION: PCR primer

<400> SEQUENCE: 1
gtatagattg tatttaataa gttaatgtaa tcc					33

<210> SEQ ID NO 2
<211> LENGTH: 30
<212> TYPE: DNA
<213> ORGANISM: Artificial
<220> FEATURE:
<223> OTHER INFORMATION: PCR primer

<400> SEQUENCE: 2
tgcaaacgat atgtagtata acttgtcaac					30

<210> SEQ ID NO 3
<211> LENGTH: 31
<212> TYPE: DNA
<213> ORGANISM: Artificial
<220> FEATURE:
<223> OTHER INFORMATION: primer

<400> SEQUENCE: 3
atatgaattc ttgagcatga cgctcaagtg c					31

<210> SEQ ID NO 4
<211> LENGTH: 33
<212> TYPE: DNA
<213> ORGANISM: Artificial
<220> FEATURE:
<223> OTHER INFORMATION: primer

<400> SEQUENCE: 4
atatcccggg gagacggtgc gttgagttaa agg					33

<210> SEQ ID NO 5
<211> LENGTH: 27
<212> TYPE: DNA
<213> ORGANISM: Artificial
<220> FEATURE:
<223> OTHER INFORMATION: primer

<400> SEQUENCE: 5
tgagctctgc gattacattg gaggctg					27

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
tgcccggggt tagttatttc attcttcg					28

<210> SEQ ID NO 7
<211> LENGTH: 32
<212> TYPE: DNA

```
<213> ORGANISM: Artificial
<220> FEATURE:
<223> OTHER INFORMATION: primer

<400> SEQUENCE: 7
cagttctaga ccttgttcag aacttcgata tg                                    32

<210> SEQ ID NO 8
<211> LENGTH: 34
<212> TYPE: DNA
<213> ORGANISM: Artificial
<220> FEATURE:
<223> OTHER INFORMATION: primer

<400> SEQUENCE: 8
cagtgagctc caggctctat aactaaaaaa tacg                                  34

<210> SEQ ID NO 9
<211> LENGTH: 32
<212> TYPE: DNA
<213> ORGANISM: Artificial
<220> FEATURE:
<223> OTHER INFORMATION: primer

<400> SEQUENCE: 9
ttgatagcat gccatgacaa atcgagctat cc                                    32

<210> SEQ ID NO 10
<211> LENGTH: 33
<212> TYPE: DNA
<213> ORGANISM: Artificial
<220> FEATURE:
<223> OTHER INFORMATION: primer

<400> SEQUENCE: 10
ttgatactgc agttaagaat aagctctgcg aca                                   33

<210> SEQ ID NO 11
<211> LENGTH: 34
<212> TYPE: DNA
<213> ORGANISM: Artificial
<220> FEATURE:
<223> OTHER INFORMATION: primer

<400> SEQUENCE: 11
ttgcgcgaat tccataaaac ttacacccgc attc                                  34

<210> SEQ ID NO 12
<211> LENGTH: 34
<212> TYPE: DNA
<213> ORGANISM: Artificial
<220> FEATURE:
<223> OTHER INFORMATION: primer

<400> SEQUENCE: 12
ttgcgcggat cccataattc acctctatga aata                                  34

<210> SEQ ID NO 13
<211> LENGTH: 32
<212> TYPE: DNA
<213> ORGANISM: Artificial
<220> FEATURE:
<223> OTHER INFORMATION: primer

<400> SEQUENCE: 13
aacatatgac aacttcaatt aaacatgcaa tg                                    32
```

```
<210> SEQ ID NO 14
<211> LENGTH: 34
<212> TYPE: DNA
<213> ORGANISM: Artificial
<220> FEATURE:
<223> OTHER INFORMATION: primer

<400> SEQUENCE: 14
aagaattcct ccttaattat tttgattgtt tttc                              34

<210> SEQ ID NO 15
<211> LENGTH: 33
<212> TYPE: DNA
<213> ORGANISM: Artificial
<220> FEATURE:
<223> OTHER INFORMATION: primer

<400> SEQUENCE: 15
aagctagcac tatttcggta aaagatgaaa atg                               33

<210> SEQ ID NO 16
<211> LENGTH: 34
<212> TYPE: DNA
<213> ORGANISM: Artificial
<220> FEATURE:
<223> OTHER INFORMATION: primer

<400> SEQUENCE: 16
aaggatccca tttacttcca ccttactttt gttc                              34

<210> SEQ ID NO 17
<211> LENGTH: 23
<212> TYPE: DNA
<213> ORGANISM: Artificial
<220> FEATURE:
<223> OTHER INFORMATION: primer

<400> SEQUENCE: 17
cctctaatgc aatgccatat tta                                          23

<210> SEQ ID NO 18
<211> LENGTH: 23
<212> TYPE: DNA
<213> ORGANISM: Artificial
<220> FEATURE:
<223> OTHER INFORMATION: primer

<400> SEQUENCE: 18
acaatgaatc acctatcgtg aca                                          23

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
agtctatcat gcgccaacaa c                                            21

<210> SEQ ID NO 20
<211> LENGTH: 22
<212> TYPE: DNA
<213> ORGANISM: Artificial
<220> FEATURE:
<223> OTHER INFORMATION: primer
```

```
<400> SEQUENCE: 20
aacctgtcgc cataatcaat aa                                        22

<210> SEQ ID NO 21
<211> LENGTH: 23
<212> TYPE: DNA
<213> ORGANISM: Artificial
<220> FEATURE:
<223> OTHER INFORMATION: primer

<400> SEQUENCE: 21
tttaaatcca gagcgtatga tca                                       23

<210> SEQ ID NO 22
<211> LENGTH: 23
<212> TYPE: DNA
<213> ORGANISM: Artificial
<220> FEATURE:
<223> OTHER INFORMATION: primer

<400> SEQUENCE: 22
cagaagaaat taagccacga gat                                       23

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
ataattatgg tgctgggcaa at                                        22

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
aaccagctaa tgcttcatcg ata                                       23

<210> SEQ ID NO 25
<211> LENGTH: 107
<212> TYPE: DNA
<213> ORGANISM: Staphylococcus aureus

<400> SEQUENCE: 25
cataattcac ctctatgaaa tattttacaa aagcaagata gatttgtata atccatatta    60
atgataatga ttcttattat caacagaatg cgggtgtaag ttttatg                 107

<210> SEQ ID NO 26
<211> LENGTH: 107
<212> TYPE: DNA
<213> ORGANISM: Staphylococcus aureus

<400> SEQUENCE: 26
```

```
gtattaagtg agatactttt ataaaatgtt ttcgttctat ctaaacatat taggtataat    60
tactattact aagaataata gttgtcttac gcccacattc aaaatac                 107

<210> SEQ ID NO 27
<211> LENGTH: 429
<212> TYPE: DNA
<213> ORGANISM: Staphylococcus aureus

<400> SEQUENCE: 27
taatgaaatc tcctgctatg gtaaaccact attaatatat ttatcaataa gtctaagttg    60
acaagttata ctacatatcg tttgcacggt tgtatcataa ttgttcaact tagattttt   120 gtatttgttg atttatcaaa ttaagtgcaa cagttcgtca cataaaattg caacagataa   180
tatcagctga attacaggga taacggtcat gctaaatggt gtcaattgta ttaatgcaaa   240
gatgatatag caatgataca ttatcagtat tttgtctaag gaaatgtgct aattgtagtc   300
ataattatta gaggaaatat atagtcatac attttagaaa tataaaaaag attgaacgtt   360
acttgacaat gataattgtt atcaataaaa taataaatga agttatacat attaaggagt   420
ggaacgatg                                                          429

<210> SEQ ID NO 28
<211> LENGTH: 429
<212> TYPE: DNA
<213> ORGANISM: Staphylococcus aureus

<400> SEQUENCE: 28
attactttag aggacgatac catttggtga taattatata aatagttatt cagattcaac    60
tgttcaatat gatgtatagc aaacgtgcca acatagtatt aacaagttga atctaaaaaa   120
cataaacaac taaatagttt aattcacgtt gtcaagcagt gtattttaac gttgtctatt   180
atagtcgact taatgtccct attgccagta cgatttacca cagttaacat aattacgttt   240
ctactatatc gttactatgt aatagtcata aaacagattc ctttacacga ttaacatcag   300
tattaataat ctcctttata tatcagtatg taaaatcttt atatttttc taacttgcaa   360 tgaactgtta ctattaacaa tagttattt attatttact tcaatatgta taattcctca   420
ccttgctac                                                          429

<210> SEQ ID NO 29
<211> LENGTH: 43
<212> TYPE: DNA
<213> ORGANISM: Staphylococcus aureus

<400> SEQUENCE: 29
agatttgtat aatccatatt aatgataatg attcttatta tca                     43
```